(12) United States Patent
DeLisa et al.

(10) Patent No.: US 8,987,173 B2
(45) Date of Patent: Mar. 24, 2015

(54) COMPOSITIONS AND METHODS FOR MONITORING AND ALTERING PROTEIN FOLDING AND SOLUBILITY

(75) Inventors: Matthew P. DeLisa, Ithaca, NY (US); Adam Charles Fisher, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 12/152,482

(22) Filed: May 14, 2008

(65) Prior Publication Data
US 2008/0287315 A1 Nov. 20, 2008

Related U.S. Application Data

(62) Division of application No. 11/194,635, filed on Aug. 1, 2005, now abandoned.

(51) Int. Cl.
| | | |
|---|---|---|
| *C40B 30/06* | (2006.01) | |
| *C12Q 1/68* | (2006.01) | |
| *C12N 15/62* | (2006.01) | |
| *C12N 15/10* | (2006.01) | |
| *C12N 15/00* | (2006.01) | |

(52) U.S. Cl.
CPC ............ *C12N 15/62* (2013.01); *C12N 15/1086* (2013.01); *C12N 15/1034* (2013.01); *C12N 15/625* (2013.01); *C07K 2319/034* (2013.01)
USPC .................. 506/10; 506/14; 435/6.1; 435/29; 435/320.1; 530/387.3

(58) Field of Classification Search
USPC ...................... 506/10, 14; 435/6.1, 29, 320.1; 530/387.3
See application file for complete search history.

(56) References Cited

U.S. PATENT DOCUMENTS

| | | | |
|---|---|---|---|
| 5,935,824 A | 8/1999 | Sqarlato | |
| 5,990,275 A | 11/1999 | Whitlow | |
| 7,252,952 B2 | 8/2007 | Lorens | |
| 2002/0110860 A1 | 8/2002 | Bron et al. | |
| 2003/0064435 A1* | 4/2003 | Weiner et al. ................ | 435/69.1 |
| 2003/0138843 A1* | 7/2003 | Waldo ............................ | 435/7.1 |
| 2003/0219870 A1* | 11/2003 | Georgiou et al. ............ | 435/69.1 |
| 2004/0077090 A1 | 4/2004 | Short | |
| 2005/0124010 A1 | 6/2005 | Short et al. | |
| 2005/0182138 A1 | 8/2005 | John et al. | |
| 2006/0078875 A1 | 4/2006 | Benkovic | |
| 2007/0026012 A1 | 2/2007 | DeLisa | |
| 2009/0220952 A1 | 9/2009 | Delisa | |
| 2009/0298089 A1 | 12/2009 | Rossner | |
| 2010/0144546 A1 | 6/2010 | Delisa | |

FOREIGN PATENT DOCUMENTS

| | | |
|---|---|---|
| WO | 9222657 | 12/1992 |
| WO | 03083056 | 10/2003 |
| WO | 2004050871 | 6/2004 |

OTHER PUBLICATIONS

Martineau et al. (Expression of an antibody fragment at high levels in the bacterial cytoplasm, 1998, Journal of Molecular Biology, vol. 280, pp. 117-127).*
Georgiou et al, "Expression of correctly folded proteins in *Escherichia coli*" Curr Opinion Biotechnolol (1996) 7, 190-197.
Maxwell et al, "A simple in vivo assay for increased protein solubility," Protein Sci (1999) 8, 1908-1911.
Waldo et al, "Rapid protein-folding assay using green fluorescent protein," Nat Biotechnolol (1999) 17, 691-695.
Cabantous et al, "Protein tagging and detection with engineered self-assembling fragments of green fluorescent protein," Nat Biotechnol (2005) 23, 102-107.
Wigley et al, "Protein solubility and folding lllonitored in vivo by structural cOlllplelllentation of a genetic lllarker protein," Nat Biotechnol (2001) 19, 131-136.
Lesley et al, "Gene Expression Response to Misfolded Protein as a Screen for Soluble Recombinant Protein" Protein Eng 15, (2002) 153-160.
Tsumoto et al, "Solubilization of active green fluorescent protein from insoluble particles by guanidine and arginine," Biochem Biophys Res Commun (2003) 312, 1383-1386.
Roodveldt et al, "Directed evolution of proteins for heterologous expression and stability," Curr Opinion Struct Biol (2005) 15, 50-56.
Wall and Pluckthun, "Effects of overexpressing folding modulators on the in vivo folding of. heterologous proteins in *Escherichia coli*," Curr Opin Biotechnol (1995) 6, 507-516.
Berks, "A common export pathway for proteins binding complex redox cofactors?," Mol Microbiol (1996) 22, 393-404.
Settles et al, "Sec-Independent Protein Translocation by the Maize Hcf106 Protein," Science (1997) 278, 1467-1470.
Weiner et al, "A Novel and Ubiquitous System for Membrane Targeting and Secretion of Cofactor-Containing Proteins," Cell (1998) 93, 93-101.
Sanders et al, "Transport of cytochrome c derivatives by the bacterial Tat protein translocation system" Mol Microbiol (2001) 41, 241-246.
Lutz et al, "A universal, vector-based system for nucleic acid reading-frame selection," Protein Eng (2002) 15, 1025-1030.
Delisa et al "Folding quality control in the export of proteins by the bacterial twin-arginine translocation pathway," Proc Natl Acad Sci USA 100, (2003) 6115-6120.
Delisa et al, "Genetic Analysis of the Twin Arginine Translocator Secretion Pathway in Bacteria," J Biol Chem (2002) 277, 29825-29831.
Collard, "Types of antibiotics and related resistance genes" (1999) Belgian Biosafety Server, http://www.antibioresistance .be/betalactamases.html (5 PGS).
Seehaus et al, "A vector for the removal of deletion mutants from antibody libraries," Gene, (1992) 114: 235-237.
Niviere et al, "Site-directed mutagenesis of the hydrogenase signal peptide consensus box prevents export of a B-lactamase fusion protein," J Gen Microbiol, (1992) 138: 2173-2183.

(Continued)

*Primary Examiner* — Sharmila G. Landau
*Assistant Examiner* — Shannon Janssen
(74) *Attorney, Agent, or Firm* — Casimir Jones S.C.

(57) ABSTRACT

The present invention relates to the fields of microbiology, molecular biology and protein biochemistry. More particularly, it relates to compositions and methods for analyzing and altering (e.g., enhancing or inhibiting) protein folding and solubility.

13 Claims, 8 Drawing Sheets

(56) References Cited

OTHER PUBLICATIONS

Smith et al, "Construction and Use of Signal Sequence Selection Vectors in *Escherichia .coli* and *Bacillus subtilis,*" J Bacteriol, (1987) 169: 3321-3328.

Delisa et al, "Genetic screen for directed evolution of soluble proteins in bacteria" Abstracts of Papers American Chemical Society, vol. 229 (Mar. 2005) p. U243.

Delisa et al, "Molecular engineering of soluble proteins directly living cells" Abstracts of Papers American Chemical Society, vol. 227, Mar. 2004, pp. U208-209.

Fisher et al, "Reprogramming the bacterial Tat system for monitoring protein folding directly in cells" Aiche Annual Meeting, Conference, Proceedings, (2004) pp. 8751.

Fisher et al, "Genetic selection for protein solubility enabled by the folding quality control feature of the twin-arginine translocation pathway" Protein Science, vol. 15, Mar. 2006 pp. 449-458.

Brondijk, et al., "NapGH components of the periplasmic nitrate reductase of *Escherichia coli* K-12: location, topology and physiological roles in quinol oxidation and redox balancing", Biochemical Journal, vol. 379, No. Part 1, Apr. 1, 2004, pp. 47-55.

Department of Biomedical Engineering: "2004-2005 Annual Report" [Online]-2005, pp. 1-60, XP002496810; The University of Texas at Austin, Retrieved from the Internet: URL: http://www.bme.utexas.edu/pdf/BME%20Annual%20Report%202004-2005.pdf> [retrieved on Sep. 23, 2008].

Dubini et al, "Assembly of Tat-dependent [NiFe] hydrogenases: identification of precursor-binding accessory proteins", Febs Letters, Elsevier, Amsterdam, NL, vol. 549, No. 1-3, Aug. 14, 2003, pp. 141-146.

European Search Report for Application No. EP06/789929; Dated Sep. 23, 2008.

International Search Report for Application No. PCT/US06/32810; Dated Mar. 6, 2007.

Strauch et al: "Towards functional genomics: A novel two-hybrid system using the TAT machinery", American Chemical Society. Abstracts of Paper. At the National Meeting, American Chemical Society, Washington DC, US, vol. 229, No. Part 1, Mar. 17, 2005, p. U228.

Arie et al., 2001, "Chaperone function of FkpA, a heat shock prolyl isomerase, in the periplasm of *Escherichia coli*", Mol Microbiol, 39: 199-210.

Bothmann and Pluckthun, 1998, "Selection for a periplasmic factor improving phage display and functional periplasmic expression", Nat Biotechnol, 16: 376-380.

Bowden et al., 1991, "Structure and morphology of protein inclusion bodies in *Escherichia coli*", Biotechnology (N Y), 9: 725-730.

Broome-Smith, 1990, "Beta-lactamase as a probe of membrane portien assembly and protein export", Molecular Microbiology, 4: 1637-1644.

DeLisa et al., 2002, Genetic analysis of the twin arginine translocator secretion pathway in bacteria, J Biol Chem, 277: 29825-29831.

Dyson et al., 2004, "Production of soluble mammalian proteins in *Escherichia coli*: identification of protein features that correslate with successful expression", BMC Biotechnol 4, 32.

Feilmeier et al., 2000, "Green fluorescent protein functions as a reporter for protein localization in *Escherichia coli*", J Bacteriol, 182: 4068-4076.

Fisher et al, 2006, "Genetic selection for protein solubility enabled by the folding quality control feature of the twin-arginine translocation pathway", Protein Science, 15: 449-458.

Frech et al., 1996, "Competition between DsbA-mediated oxidation and conformational folding of RTEM1 beta-lactamase", Biochemistry, 35: 11386-11395.

Missiakas et al., 1996, "New components of protein folding in extracytoplasmic compartments of *Escherichia coli* SurA, FkpA and Skp/OmpH", Mol Micorbiol, 21: 871-884.

Schierle, 2003, "The DsbA Signal Sequence Directs Efficient, Cotranslational Export of Passanger Proteins to the *Escherichia Coli* Periplasm via the Signal Recognition Particle Pathway", J Bacteriol., 185: 5706-5713.

Sone et al., 1997, Roles of disulfide bonds in bacterial alkaline phosphatase, J Biol Chem, 272: 6174-6178.

Steiner et al., 2006, "Signal sequences directing cotranslational translocation expand the range of proteins amenable to phage display", Nat Biotechnol, 24: 823-831.

Tomoyasu et al., 2001, "Genetic dissection of the roles of chaperones and proteases in protein folding degradation in the *Escherichia coli* cytosol", Mol Microbiol, 40: 397-413.

Villaverde and Carrio, 2003, "Protein aggregation in recombinant bacteria: biological role of inclusion bodies", Biotechnol Lett, 25: 1385-1395.

International Search Report for Application No. PCT/US06/29998; Dated Aug. 1, 2008.

European Search Report for Application No. EP06/789138; Dated Apr. 21, 2009.

International Search Report for Application No. PCT/US08/50991; Dated Aug. 12, 2008.

Tullman-Ercek, Danielle et al., "Export pathway selectivity of *Escherichia coli* twin arginine translocation signal peptides," Journal of Biological Chemistry, vol. 282, No. 11, Mar. 2007, pp. 8309-8316.

Gerth, M.L., et al, "A second-generation system for unbiased reading frame selection," Protein Engineering, Design &Selection, vol. 17, No. 7, pp. 595-602 (2004).

Lutz, S., et al., "A Universal, Vector-Based System for Nucleic Acid Reading-Frame Selection," Protein Engineering, vol. 15, No. 12, pp. 1025-1030 (2002).

Wurth, C., et al., "Mutations that Reduce Aggregation of the Alzheimer's Aβ42 Peptide: an Unbiased Search for the Sequence Determinants of Aβ Amyloidogenesis," J. Mol. Biol. (2002) 319, pp. 1279-1290.

Choi, J.H., and Lee, S.Y., "Secretory and Extracellular Production of Recombinant Proteins Using *Escherichia coli,*" App. Microbiol. (2004) 64: pp. 625-635.

Shih, Yan-Ping, et al., "High-Throughput Screening of Soluble Recombinant Proteins," Protein Science (2002), 11: pp. 1714-1719.

Philibert Pascal et al, "Directed evolution of single-chain Fv for cytoplasmic expression using the [beta]-galactosidase complementation assay results in proteins highly susceptible to protease degradation and aggregation," Microbial Cell Factories, Biomed Central, London, NL, vol. 3, No. 1, Dec. 17, 2004, p. 16.

Cattaneo, Antonio, et al., "The Selection of Intracellular Antibodies," TIBTECH (1999) vol. 17, pp. 115-120.

\* cited by examiner

US 8,987,173 B2

COMPOSITIONS AND METHODS FOR MONITORING AND ALTERING PROTEIN FOLDING AND SOLUBILITY

The present application is a divisional application of U.S. patent application Ser. No. 11/194,635, filed Aug. 1, 2005 now abandoned.

GOVERNMENT SUPPORT

This invention was made with government support under grant number BES-0449080, awarded by the National Science Foundation. The government has certain rights in the invention.

FIELD OF THE INVENTION

The present invention relates to the fields of microbiology, molecular biology and protein biochemistry. More particularly, it relates to compositions and methods for analyzing and altering (e.g., enhancing or inhibiting) protein folding and solubility.

BACKGROUND OF THE INVENTION

The expression of heterologous proteins represents a cornerstone of the biotechnology enterprise. Unfortunately, many commercially important proteins misfold and aggregate when expressed in a heterologous host (See, e.g., Makrides, Microbiol Rev 60, 512-538 (1996); Baneyx and Mujacic, Nat Biotechnol 22, 1399-1408 (2004); Georgiou and Valax, Curr Opin Biotechnol 7, 190-197 (1996)). Similarly, protein misfolding and aggregation is the pathological hallmark of more than a dozen diseases including Alzheimer's (See, e.g., Radford et al., Cell 97, 291-298 (1999); Ross and Poirier, Nat Med 10 Suppl, S10-17 (2004)). As if this weren't enough, existing biochemical means for assessing the tendency of proteins to misfold and aggregate are tedious. As a result, screening for constructs and/or conditions that favor solubility is inefficient and genetic selection of folded structures has not been forthcoming.

Development of a robust assay for in vivo protein folding and solubility has been challenging for researchers because of limitations on detecting and reporting the solubility of a protein. Existing systems for monitoring protein misfolding in vivo have capitalized on the observation that a misfolded target protein will often co-translationally induce improper folding of a C-terminally fused reporter protein (See, e.g., Maxwell et al., Protein Sci 8, 1908-1911 (1999); Waldo et al., Nat Biotechnol 17, 691-695 (1999)) or protein fragment (See, e.g., Cabantous et al., Nat Biotechnol 23, 102-107 (2005); Wigley et al., Nat Biotechnol 19, 131-136 (2001)) or will induce a specific gene response (See, e.g., Lesley et al., Protein Eng 15, 153-160 (2002)). This fusion approach is often problematic as certain reporter proteins can remain active even when the target protein to which they are fused aggregates or forms inclusion bodies (See, e.g., Tsumoto et al., Biochem Biophys Res Commun 312, 1383-1386 (2003)) while the gene expression response is limited by its indirect connection to the folding process.

Additionally, existing assays for protein expression in soluble form are tedious, usually requiring lysis and fractionation of cells followed by protein analysis by SDS-polyacrylamide gel electrophoresis. Using these traditional approaches, screening for protein constructs and/or physiological conditions yielding improved solubility is inefficient, and genetic selection nearly impossible.

Thus, there remains a need for new compositions and methods (e.g., assays) for monitoring, altering and/or selecting folded and soluble proteins (e.g., in vivo or in vitro). Such methods and compositions should be able to rapidly improve the soluble yield of a target protein by optimizing its primary sequence (e.g., through genetic selection) (See, e.g., Roodveldt et al., Curr Opin Struct Biol 15, 50-56 (2005)) or its cellular folding environment (See, e.g., Wall and Pluckthun, Curr Opin Biotechnol 6, 507-516 (1995)). Furthermore, such methods and compositions should be readily amenable to assay for agents (e.g., pharmaceuticals, drugs, small molecules, etc.) that either promote the folding/inhibit the aggregation of proteins associated with human disease (e.g. Alzheimer's Aβ42 peptide) (See, e.g., Williams et al., Proc Natl Acad Sci USA (2005)), or, on the contrary, agents that alter proper folding and induce aggregate formation (e.g., that could be used as antibiotics).

SUMMARY OF THE INVENTION

The present invention relates to the field of protein biochemistry. More particularly, it relates to compositions and methods for analyzing and altering (e.g., enhancing or inhibiting) protein folding and solubility.

Accordingly, in some embodiments, the present invention provides a composition comprising a fusion protein, wherein the fusion protein comprises a Tat signal sequence, a target protein and a marker protein. In some embodiments, the Tat signal sequence is TorA. The present invention is not limited by the Tat signal sequence (e.g., peptidte) used. Indeed, a variety of signal sequences are contemplated to be useful in the present invention including, but not limited to, CueO, DmsA, FdnG, FdoG, HyaA, NapA, Sufl, TorA, WcaM, YagT, YcbK, YcdB, YdhX, YnfE and others described in Example 5 (e.g., in Table 2). The present invention further provides a method for identifying signal peptides that find use in the present invention comprising a bioinformatics algorithm (e.g., a Hidden Markov Model). In some embodiments, the marker protein is an antibiotic resistance protein. In a preferred embodiment, the antibiotic resistance protein is TEM1 β-lactamase.

The present invention also provides a composition comprising a nucleic acid sequence encoding a fusion protein, wherein the fusion protein comprises a Tat signal sequence, a target protein and a marker protein. In some embodiments, the sequence is expressed constitutively. In some embodiments, the sequence is operatively linked to a promoter. In some embodiments, the promoter is present within an expression vector. In some embodiments, the promoter is lac, pho (e.g. phoA), tac, trc, trp, tet, araBAD, λ $P_L$, T3, T7, T7-lac and SP6. In some embodiments, the nucleic acid sequence comprises at least one sequence encoding one amino acid sequence, operatively linked to a second sequence encoding a second amino acid sequence, operatively linked to a third sequence encoding a third amino acid sequence, wherein the sequences are translated as a contiguous amino acid sequence in vivo or in vitro.

The present invention also provides a host cell comprising a nucleic acid sequence, the nucleic acid sequence encoding a fusion protein, wherein the fusion protein comprises a Tat signal sequence, a target protein and a marker protein. In some embodiments, the host cell is a bacterial cell. In some preferred embodiments, the host cell is E. coli strain MC4100. The present invention is not limited by the type of host cell. Indeed, a variety of host cells are contemplated to be useful in the present invention including, but not limited to, a species of bacteria selected from the group consisting of

*Acetobacter, Actinomyces, Aerobacter, Agribacterium, Azotobacter, Bacillus, Bacteroides, Bordetella, Brucella, Chlamydia, Clostridium, Corynebacterium, Erysipelothrix, Escherichia, Francisella, Fusobacterium, Haemophilus, Klebsiella, Lactobacillus, Listeria, Mycobacterium, Myxococcus, Neisseria, Nocardia, Pasteurella, Proteus, Pseudomonas, Rhizobium, Rickettsia, Salmonella, Serratia, Shigella, Spirilla, Spirillum, Staphylococcus, Streptococcus, Streptomyces, Trepanema, Vibrio, Vibrio,* and *Yersinia.*

The present invention also provides a method for analyzing protein solubility and/or folding comprising providing a nucleic acid sequence encoding a fusion protein, wherein the fusion protein comprises a Tat leader signal, a target protein, and a marker protein; expressing the fusion protein in a host cell; and correlating the ability of the host cells to grow under selective pressure with the solubility and/or folding of the target protein. In preferred embodiments, the growth of the host cells under the selective pressure is indicative of a soluble target protein. In some embodiments, the fusion protein comprises a TorA signal peptide. In some embodiments, the marker protein is TEM1 β-lactamase. In some embodiments, the growth rate of the host cells provides qualitative information regarding target protein solubility (e.g., methods of the present invention are capable of providing information regarding a range of different levels of target protein solubility). For example, in some embodiments, host cells comprising a fusion protein incapable of growing under a selective pressure (e.g., in the presence of ampicillin) are indicative of a target protein that has poor to no solubility within the host cell. In some embodiments, host cells comprising a fusion protein that grow well under a selective pressure (e.g., in the presence of ampicillin) are indicative of a target protein that is soluble within the host cell. In further embodiments, host cells comprising a fusion protein that display an intermediate level of growth (e.g., somewhere between no growth and those that grow well) are indicative of a target protein that has an intermediate/moderate level of solubility within the host cell.

The present invention also provides a method for screening for mutations in a target protein sequence that alters solubility and/or folding of the target protein, comprising: providing a nucleic acid sequence encoding a fusion protein, wherein the fusion protein comprises a Tat leader signal, a target protein, and a marker protein; introducing one or more mutations into a region of the target protein of the nucleic acid sequence; expressing the fusion protein (e.g., comprising one or more mutations) in a host cell; and correlating the ability of the host cells to grow under selective pressure with the solubility and/or folding of the target protein. In some embodiments, host cells comprising a fusion protein incapable of growing under a selective pressure (e.g., in the presence of ampicillin) are indicative of a mutant target protein that has poor to no solubility within the host cell. In some embodiments, host cells comprising a fusion protein that grow well under a selective pressure (e.g., in the presence of ampicillin) are indicative of a mutant target protein that is soluble within the host cell. In further embodiments, host cells comprising a fusion protein that display an intermediate level of growth (e.g., somewhere in between no growth and those that grow well) are indicative of a mutant target protein that has an intermediate/moderate level of solubility within the host cell. In some embodiments, the method is used to screen a library of host cells comprising the fusion proteins comprising mutations in the target protein (e.g., scanning mutagenesis can be utilized to systematically alter the nucleic acid sequence encoding a fusion protein, resulting in a large number of unique mutant target proteins, each of which can individually, or in combination, be expressed in a host cell).

The present invention also provides a method for screening for mutations in a host cell that alters solubility and/or folding of a target protein, comprising: providing a nucleic acid sequence encoding a fusion protein, wherein the fusion protein comprises a Tat leader signal, the target protein, and a marker protein; expressing the fusion protein in a host cell; wherein the host cell has undergone mutagenesis; and correlating the ability of the host cells comprising the fusion protein to grow under selective pressure with the solubility and/or folding of the target protein. In some embodiments, an increase in growth correlates with a host cell environment that improves target protein solubility.

The present invention further provides a method of screening candidate agents (e.g., a small molecule library, pharmaceuticals, drugs, chemicals or other compounds) for the ability to alter the solubility and/or folding of a target protein, comprising, providing a nucleic acid sequence encoding a fusion protein, wherein the fusion protein comprises a Tat leader signal, a target protein, and a marker protein; expressing the fusion protein in a host cell; contacting the host cell with a candidate substance; and correlating host cell growth in the presence or absence of the candidate substance with the solubility and/or folding of the target protein.

The present invention also provides methods for analyzing the ability of candidate proteins (e.g., chaperones or binding partners), protein fragments and/or peptides to alter the solubility and/or folding of a target protein comprising, providing a nucleic acid sequence encoding a fusion protein, wherein the fusion protein comprises a Tat leader signal, a target protein, and a marker protein; expressing the fusion protein in a host cell; co-expressing the candidate protein, protein fragment and/or peptide; and correlating host cell growth in the presence or absence of the candidate protein, protein fragment and/or peptide with the solubility and/or folding of the target protein.

DESCRIPTION OF THE DRAWINGS

FIG. 3(B) shows the relative periplasmic Bla activity as determined by the rate of nitrocefin hydrolysis (gray bars) and relative growth rate as determined by 96-well plate liquid growth assays (white bars). FIG. 3(C) shows growth on solid medium by spot plating 5 μL of an equivalent number of cells on LB agar supplemented with 100 μg/mL ampicillin. FIG. 3(D) shows growth on solid medium by spot plating 5 μL of an equivalent number of cells on LB agar supplemented with 25 μg/mL chloramphenicol.

FIG. 4(A) shows growth of MC4100 cells on LB agar supplemented with 100 μg/mL ampicillin expressing GST, TrxA, Top7, GFP, p53, NY-ESO1, TraR or PhoA in the target position of pTMB. Each spot represents 5 μL of an equivalent number of overnight grown cells. FIG. 4(B) shows relative growth rate of MC4100 cells as determined by 96-well plate liquid growth assays.

DEFINITIONS

Figure 1:
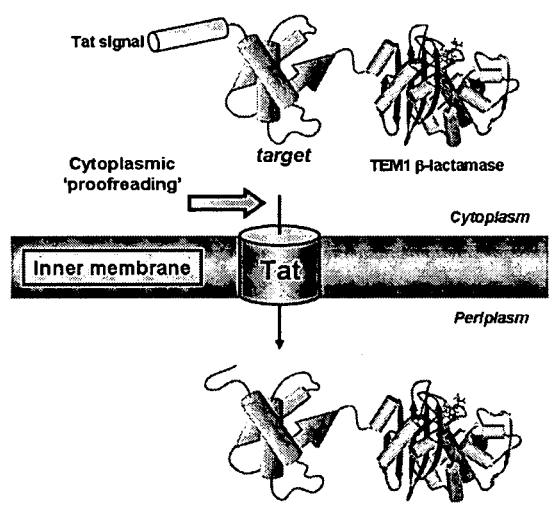
FIG. 1 depicts a cartoon of the Tat pathway's ability to monitor protein folding and/or solubility.

To facilitate an understanding of the invention, a number of terms are defined below.

As used herein, the term "target protein" when used in reference to a protein or nucleic acid refers to a protein or nucleic acid encoding a protein of interest for which solubility and/or folding is to be analyzed and/or altered of the present invention. The term "target protein" encompasses both wild-type proteins and those that are derived from wild type proteins (e.g., variants of wild-type proteins or polypeptides, or, chimeric genes constructed with portions of target protein coding regions), and further encompass fragments of a wild-type protein. Thus, in some embodiments, a "target protein" is a variant or mutant. The present invention is not limited by the type of target protein analyzed.

As used herein, the term "fusion protein" refers to a polypeptide sequence, and nucleic acid molecules encoding the same, comprising a Tat signal peptide, a target protein and a marker protein. Multiple Tat signal peptides/leader sequences are known in the art (See, e.g., DeLisa et al., Proc. Natl. Acad. Sci. 100, 6115 (2003); and Example 5) and are contemplated to be useful in the present invention. The present invention contemplates that the fusion protein may be under the control of an inducible, a constitutively active, or other promoter.

The invention is not limited by the type of marker protein. As used herein, the terms "marker protein" or "selectable marker" refer to a nucleic acid sequence (e.g., gene) that encodes an activity (e.g., an enzymatic activity) that confers the ability to grow in medium lacking what would otherwise be an essential nutrient (e.g. the HIS3 gene in yeast cells); in addition, a "marker protein" or "selectable marker" may confer resistance to an antibiotic or drug upon the cell in which the selectable marker is expressed. The present invention contemplates the use of a marker protein or selective marker in plasmids comprising nucleic acid sequences encoding a fusion protein, as well as use of a marker protein or selective marker within the nucleic acid sequence encoding the fusion protein itself. For example, host cells comprising a nucleic acid encoding a fusion protein may grow in a selective environment (e.g., when exposed to an antibiotic) because the nucleic acid encoding a fusion protein (e.g., comprising a marker protein) encodes activity (e.g., β-lactamase activity) that confers resistance to the antibiotic.

As used herein, the term "instructions for using said kit for said monitoring the folding and/or solubility of a target protein" includes instructions for using the reagents contained in the kit for monitoring the solubility and/or folding (e.g., through the growth of host cells in the presence of a selectable marker) of a target protein.

As used herein, the term "solubility profile" refers to the solubility and/or folding properties of a target protein, wherein the solubility and/or folding properties of a target protein are monitored by measuring the ability of host cells, comprising a fusion protein that comprises a target protein, to grow in the presence of a drug, antibiotic, or other selective pressure (e.g., in the presence of ampicillin). In preferred embodiments, the ability of host cells to grow in the presence of the drug, antibiotic, or other selective pressure is indicative of the solubility of the target protein, whereas, the absence of host cell growth is indicative of the insolubility of the target protein. The solubility profiles of the present invention find use in, among other things, the characterization of target protein solubility and/or folding, mutant target protein solubility and/or folding, and the effect of candidate compositions on the solubility and/or folding of a target protein. In preferred embodiments, a solubility profile detects intermediate ranges of solubility (e.g., via correlating the relative growth rate of host cells comprising a fusion protein of the present invention in the presence of a drug, antibiotic, or other selective pressure with the relative periplasmic expression, i.e., the solubility, of the fusion protein comprising the target protein and a marker protein).

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of a sample (e.g., a nucleic acid encoding a fusion protein of the present invention) to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, RNA (e.g., including but not limited to, mRNA, tRNA and rRNA) or precursor. The polypeptide, RNA, or precursor can be encoded by a full length coding sequence or by any portion thereof. The term also encompasses the coding region of a structural gene and the sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the terms "target protein gene" or "target protein genes" refer to the full-length target protein sequence. However, it is also intended that the term encompass fragments of the target protein sequences, mutants of the target protein sequences, as well as other domains within the full-length target protein nucleotide sequences. Furthermore, the terms "target protein nucleotide sequence" or "target protein polynucleotide sequence" encompasses DNA, cDNA, and RNA (e.g., mRNA) sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics (e.g., increased or decreased solubility) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc.). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, the sequence 5'-A-G-T-3', is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Complementarity can include the formation of base pairs between any type of nucleotides, including non-natural bases, modified bases, synthetic bases and the like.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_M$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_M$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization (1985)). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less. "High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.1% SDS, 5×Denhardt's reagent (50×Denhardt's contains per 500 ml: 5 g Ficoll (Type 400, Pharamcia), 5 g BSA (Fraction V; Sigma)) and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math. 2: 482 (1981)) by the homology alignment algorithm of Needleman and Wunsch (Needleman and Wunsch, J. Mol. Biol. 48:443 (1970)), by the search for similarity method of Pearson and Lipman (Pearson and Lipman, Proc. Natl. Acad. Sci. (U.S.A.) 85:2444 (1988)), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the fusion protein sequences of the compositions claimed in the present invention (e.g., a target protein sequence).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein the term "coding region" when used in reference to a structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets, which specify stop codons (i.e., TAA, TAG, TGA).

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (e.g., 10 nucleotides, 20, 30, 40, 50, 100, 200, etc.).

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. The present invention is not limited to naturally occurring protein molecules. For example, the present invention contemplates synthesis of fusion proteins comprising multiple regions of unique polypeptide sequences (e.g., a Tat leader sequence, a target protein sequence, and marker protein sequence).

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "native protein" is used to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31-9.58 (1989)).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 (1989)).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 (1973)), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The term "candidate agent" may be any substance that potentially inhibits or enhances protein folding and/or solubility, including, but not limited to, any chemical entity, pharmaceutical, drug, and the like (e.g., a small molecule or compound). Candidate agents may include fragments or parts of naturally-occurring proteins or compounds, or may be found as active combinations of known proteins or compounds, which are otherwise inactive. It is to be understood that candidate agents comprise both known and potential solubility inhibiting or enhancing agents. A candidate agent can be determined to be capable of altering target protein solubility and/or folding using the methods of the present invention.

As used herein, the term "host cell" refers to any cell, whether located in vitro or in vivo, that can be, or has been, a recipient for or incorporates exogenous nucleic acid sequences (e.g., vectors comprising fusion protein sequence), polynucleotides and/or proteins of the present invention. It is also meant to include progeny of a single cell, and the progeny may not necessarily be completely identical (e.g., in morphology or in genomic or total DNA complement) to the original parent cell due to natural, accidental, or deliberate mutations. The cells may be eukaryotic or prokaryotic and include, but are not limited to bacterial cells (e.g., *E. coli*) yeast cells, mammalian cells, avian cells, amphibian cells, plant cells, fish cells, and insect cells).

DETAILED DESCRIPTION OF THE INVENTION

While genetic engineering technology has provided the capability to modulate the expression of virtually any protein-encoding polynucleotide in a selected cell, it has been observed that purposeful manipulation of protein production in genetically modified cells often leads to the formation of incorrectly folded, biologically inactive protein molecules. In many cases, these mis-folded protein products form insoluble protein aggregates within the cytoplasm of the cell. Whether the purpose of the manipulation of expression of a target protein is to alter the phenotype of the cell, to provide a source of biologically active protein, or a source of protein that is suitable for structural analysis, these insoluble aggregates are biologically inactive, difficult to purify and difficult to refold into an active configuration.

In bacterial cells, specific targeting and transport mechanisms are required to move proteins along transport pathways from their site of synthesis in the cytoplasm to their eventual destination. One such pathway, the twin-arginine translocation (Tat) pathway, is capable of delivering folded proteins across biological membranes via translocation machinery minimally comprised of the TatABC proteins (See, e.g., Berks, Mol Microbiol 22, 393-404 (1996); Settles et al., Science 278, 1467-1470 (1997); Weiner et al., Cell 93, 93-101 (1998)). Recent in vivo studies demonstrate the ability of the Tat pathway to selectively discriminate between properly folded and misfolded proteins in vivo and suggest the existence of a folding quality control mechanism intrinsic to the process (See, e.g., Sanders et al., Mol Microbiol 41, 241-246 (2001); Lutz et al., Protein Eng 15, 1025-1030 (2002); DeLisa et al., Proc Natl Acad Sci USA 100, 6115-6120 (2003)).

The present invention exploits the Tat pathway and provides a general platform for screening protein solubility. Thus, compositions and methods of the present invention are capable of providing information regarding protein sequences that are prone to off-pathway intermediates or aggregation for reasons unrelated to disulfide bond formation or cofactor insertion. Providing information regarding these steps is crucial because early events during protein expression and folding that lead to thermodynamically or kinetically trapped intermediates often supercede disulfide bond formation, which is typically a later step in the folding process.

Several diseases, such as Alzheimer's disease, Parkinson's disease, Huntington's disease, and others are thought to be the result of, or associated with protein misfolding in vivo. In certain embodiments, the present invention provides a method for assaying for the presence of target protein misfolding in a living cell (e.g., a bacterial cell).

Proteins expressed through recombinant means often misfold, particularly in prokaryotic host cells that lack the processing machinery of an eukaryotic cell. When a protein misfolds, it often becomes less soluble, and may precipitate in the cell as an inclusion body. Additionally, mutations in naturally occurring proteins increase the rate of misfolding when endogenously expressed, as well as when exogenously expressed in a recombinant host cell.

Accordingly, the present invention provides cells, compositions, and methods for determining whether a host cell expresses a polypeptide of interest in soluble or insoluble form. In some embodiments, the present invention exploits the ability of the Tat pathway to report protein folding and solubility in bacterial cells (e.g. *E. coli*) (See, e.g., FIG. 1). In preferred embodiments, the present invention provides a fusion protein, and nucleic acids encoding the same, wherein the fusion protein comprises a Tat signal peptide (e.g. ssTorA), a target protein and a marker protein (e.g., an antibiotic resistance marker, See, e.g., Examples 1-4). In some embodiments, the fusion protein is inducible. In some embodiments, the fusion protein is constitutively expressed. Various nucleic acid constructs useful for expression of the fusion protein of the present invention are described below and in Examples 1-4.

An aspect of the present invention is the discovery that multiple peptides, polypeptides or proteins may be joined to a target protein (e.g., to create a fusion protein), wherein folding of the target protein is monitored by the growth, or lack of growth, of host cells comprising the fusion protein. The target protein may have the same length or amino acid sequence as the endogenously produced protein, if such protein exists. In other embodiments, the target protein may be a truncated protein, protein domain or protein fragment of a larger peptide chain. For example, the target protein may comprise a fragment of a membrane embedded or otherwise hydrophobic protein.

In some embodiments, fusion proteins are produced by operatively linking at least one nucleic acid encoding at least one amino acid sequence to at least a second nucleic acid encoding at least a second amino acid sequence, so that the encoded sequences are translated as a contiguous amino acid sequence either in vitro or in vivo. Fusion protein design and expression is well known in the art, and methods of fusion protein expression are described herein, and in references, such as, for example, U.S. Pat. No. 5,935,824, incorporated herein by reference in its entirety for all purposes. In some embodiments, linkers are used to join the various portions of the fusion protein. One such linker is another peptide, such as described in U.S. Pat. No. 5,990,275, incorporated herein by reference in its entirety for all purposes. In some embodiments, the fusion protein, and nucleic acids encoding the same, comprises a Tat signal peptide, a target protein and a marker protein (e.g., an antibiotic resistance marker), wherein the Tat signal is N-terminal to the target protein that is N-terminal to the marker protein (See, e.g., Example 1). However, it is contemplated that the portions of the fusion proteins may be assembled in any order (e.g., the target protein is to the N-terminus of the marker protein that is to the N-terminus of the Tat signal peptide).

The present invention is not limited by the type of target protein assayed, nor to the type of Tat leader signal or marker protein used. Indeed, the present invention can be utilized characterize or monitor the solubility and/or folding of any protein, and the ability of other factors (e.g., small molecules, pharmaceuticals, etc.) to alter (e.g., enhance or inhibit) the solubility and/or folding of the target protein.

The present invention is not limited to any particular Tat signal peptide. For example, during development of the present invention, signal peptides capable of Tat transport were identified. (See, e.g., Example 5) Thus, a variety of signal peptides are contemplated to be useful in the present invention including, but not limited to, those sequences described in Example 5, and those described in DeLisa et al., Proc. Natl. Acad. Sci. 100, 6115-6120 (2003)).

Studies conducted during the development of the present invention demonstrate that compositions and methods of the present invention reliably monitor protein solubility and/or folding across a vast range of biologically relevant target proteins (See, e.g., Examples 3-4). For example, in some embodiments, a target protein may be a wild-type (e.g., full length) protein or may be a peptide fragment thereof (e.g., a polypeptide sequence of 4 or more amino acids, or preferably 10 or more amino acids). In some embodiments, the polypeptides are "heterologous," meaning that they are foreign to the host cell being utilized (e.g., a human protein produced by a CHO cell, or a yeast polypeptide produced by a mammalian cell, or a human polypeptide produced from a human cell line that is not the native source of the polypeptide). Thus, the target protein may be any protein of interest for which the solubility and/or folding is to be analyzed. For example, the target protein may be Alzheimer's amyloid peptide (Aβ), SOD1, presenillin 1 and 2, renin, α-synuclein, amyloid A, amyloid P, activin, anti-HER-2, bombesin, enkephalinase, protease inhibitors, therapeutic enzymes, α1-antitrypsin, mammalian trypsin inhibitor, mammalian pancreatic trypsin inhibitor, calcitonin, cardiac hypertrophy factor, cardiotrophins (such as cardiotrophin-1), CD proteins (such as CD-3, CD-4, CD-8 and CD-19), CFTR, CTNF, DNase, human chorionic gonadotropin, mouse gonadotropin-associated peptide, cytokines, transthyretin, amylin, lipoproteins, lymphokines, lysozyme, a growth hormone (including human growth hormone), bovine growth hormone, growth hormone releasing factor, parathyroid hormone, thyroid stimulating hormone, growth factors, brain-derived neurotrophic growth factor, epidermal growth factor (EGF), fibroblast growth factor (such as α FGF and β FGF), insulin-like growth factor-I and -II, des(1-3)-IGF-I (brain IGF-I), insulin-like growth factor binding proteins, nerve growth factor (such as NGF-β, platelet-derived growth factor (PDGF), vascular endothelial growth factor (VEGF), receptors for growth hormones or growth factors, transforming growth factor (TGF) (such as TGF-α, TGF-β1, TGF-β2, TGF-β3, TGF-β4 or TGF-β5), neurotrophic factors (such as neurotrophin-3, -4, -5, or -6), gelsolin, glucagon, kallikreins, mullerian-inhibiting substance, neurotrophic factors, p53, protein A or D, prorelaxin, relaxin A-chain, relaxin B-chain, rheumatoid factors, rhodopsin, a serum albumin (such as human serum albumin), inhibin, insulin, insulin chains, insulin A-chain, insulin β-chain, insulin receptor, proinsulin, luteinizing hormone, integrin, interleukins (ILs) (such as IL-1 to IL-10, IL12, IL-13), erythropoietin, thrombopoietin, fibrillin, follicle stimulating hormone, clotting factors (such as factor VIIIC, factor IX, tissue factor, and von Willebrands factor, anti-clotting factors (such as Protein C, atrial naturietic factor, lung surfactant), a plasminogen activator (such as human tissue plasminogen activator or urokinase), thrombin, tumor necrosis factor-α or β, α-ketoacid dehydrogenase, addressins, bone morphogenetic proteins (BMPs), collagen, colony stimulating factors (CSFs) (such as M-CSF, GM-CSF and G-CSF), decay accelerating factor, homing receptors, interferons (such as interferon-α, -β and -γ), keratin, osteoinductive factors, PRNP, regulatory proteins, superoxide dismutase, surface membrane proteins, transport proteins, T-cell receptors, viral antigens such as a portion of the AIDS envelope, immunoglobulin light chain, antibodies, antibody fragments (such as single-chain Fv fragment (scFv), single-chain antibody (scAb), FAB antibody fragment, diabody, triabody, fluorobody), antigens such as gp120(IIIb) immunotoxins, atrial natriuretic peptide, seminal vesicle exocrine protein, β2-microglobulin, PrP, precalcitonin, ataxin 1, ataxin 2, ataxin 3, ataxin 6, ataxin 7, huntingtin, androgen receptor, CREB-binding protein, gp120, p300, CREB, API, ras, NFAT, jun, fos, dentaorubral pallidoluysian atrophy-associated protein, a microbial protein (e.g., maltose binding protein, ABC transporter, glutathione S transferase, thioredoxin, β-lactamase), green fluorescent protein, red fluorescent protein, or derivatives or active fragments or genetic variants of any of the peptides listed above. The polypeptides may be native or mutated polypeptides, and preferred sources for such mammalian polypeptides include human, bovine, equine, porcine, lupine and rodent sources, with human proteins being particularly preferred.

In some embodiments, the marker protein is all or a portion of a drug resistant marker (e.g., an antibiotic resistance protein). In some embodiments, the antibiotic resistant protein is encoded by all or a portion of the aada gene, the streptomycin phosphotransferase (SPT) gene, the neomycin phosphotransferase gene (NPTII), the hygromycin phosphotransferase (HPT) gene, or genes encoding resistance to ampicillin, tetracycline, or chloramphenicol. In some embodiments, the marker protein is an enzyme or a portion of an enzyme that can be readily assayed (such as alkaline phosphatase, β-galactosidase, β-glucoronidase, chloramphenicol acetyl transferase (CAT), DHFR, luciferase). In some embodiments, the marker protein is a fluorescent protein (such as green fluorescent protein (GFP), GFP-SsrA (See, e.g., DeLisa et al., 2002), yellow fluorescent protein (YFP), cyan fluorescent protein (CFP), blue fluorescent protein (BFP), red fluorescent protein (DsRed, mRFP) and genetic variants thereof).

In preferred embodiments, the marker protein is mature TEM1 β-lactamase protein (Bla). Because Bla confers antibiotic resistance on Gram-negative bacteria when present in the periplasmic space, it minimally acts to report the cellular localization of a protein chimera, not its solubility. Although identification of a mechanism is not necessary to practice the present invention, and the present invention is not limited to any particular mechanism, in some embodiments, by relying on the native Tat pathway to determine the folding status of a target protein, the present invention overcomes problems present in the prior art (e.g., fusion constructs that possess peptides of proteins of interest and residually active marker peptides) by revealing the genuine folding and solubility effects without the plague of false positives. Furthermore, since Tat-targeted proteins have a significant residence time in the cytoplasm prior to transport, the present invention is amenable to studying slow misfolding or aggregation events that may escape detection by co-translational folding schemes.

Fusion protein nucleic acids of the present invention may comprise additional sequences, such as coding sequences within the same transcription unit, controlling elements such as ribosome binding sites, and polyadenylation sites, additional transcription units under control of the same or a different promoter, sequences that permit cloning, expression, and transformation of a host cell, and any such construct as may be desirable to provide in embodiments of the invention.

The fusion protein nucleic acids may also include a polynucleotide sequence that encodes a molecular tag that can facilitate separation of a host cell that expresses the fusion protein from a host cell that does not express the fusion protein. For example, an epitope for an antibody can function as a molecular tag; cells that express the fusion protein can then be immobilized by contacting the cells with a solid support to which is attached antibodies that specifically recognize the epitope. Other suitable molecular tags are well known to those of skill in the art, and include, for example, a poly-histidine tag, or a FLAG peptide.

For example, in some embodiments, the fusion protein construct may comprise a nucleic acid sequence encoding a FlAsH binding motif (See, e.g., Example 7). The use of a FlAsH tag permits a greater range (e.g., nearly unlimited range) of potential attachment sites to a target protein (e.g., on the N-terminus, C-terminus or even embedded within the target protein—e.g., when C-terminal and/or N-terminal regions are being analyzed for the ability to interact with other proteins that may alter target protein solubility—e.g., chaperone proteins). The use of such tags enables one to identify a target protein from other proteins within a host cell.

The polynucleotides and sequences embodied in this invention can be obtained using, among other methods, chemical synthesis, recombinant cloning methods, PCR, or any combination thereof. PCR technology is the subject matter of U.S. Pat. Nos. 4,683,195; 4,800,159; 4,754,065; and 4,683,202 and described in PCR: THE POLYMERASE CHAIN REACTION (Mullis et al. eds, Birkhauser Press, Boston (1994)) and references cited therein. Alternatively, one of skill in the art can use the sequences provided herein, or available from other sources (e.g., www.ncbi.nlm.nih.gov) and a commercial DNA synthesizer, PCR, or other molecular biological techniques to synthesize or otherwise attain the nucleic acid sequence (e.g., DNA sequence) of any target protein of interest.

Once the target protein of interest, marker protein and Tat leader sequence are chosen, they may be operatively expressed in a recombinant vector. The vector may be expressed in vitro or in vivo for analyzing and/or altering target protein solubility and/or folding. As used herein, the term "vector" is used in reference to nucleic acid molecules that transfer nucleic acid (e.g., DNA) segment(s) from one cell to another. The term "vehicle" is sometimes used interchangeably with "vector." A nucleic acid sequence can be "exogenous" or "heterologous," which means that it is foreign to the cell into which the vector is being introduced or that the sequence is homologous to a sequence in the cell but in a position within the host cell nucleic acid in which the sequence is ordinarily not found. Vectors include, but are not limited to, plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1989 and Ausubel et al., 1994, both incorporated herein by reference.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. In addition to control sequences that govern transcription and translation, vectors and expression vectors may contain nucleic acid sequences that serve other functions as well, some of which are described below.

Promoters and Enhancers.

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence (e.g., a nucleic acid sequence encoding a fusion protein of the present invention) to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," e.g., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (see U.S. Pat. No. 4,683,202, U.S. Pat. No. 5,928,906, each incorporated herein by reference). It is further contemplated that control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment (e.g., comprising nucleic acid encoding a fusion protein of the present invention) in the cell type, organelle, and organism chosen for expression. Those of skill in the art of microbiology and molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct the desired level expression of the introduced DNA segment comprising a target protein of the present invention (e.g., high levels of expression that are advantageous in the large-scale production of recombinant proteins and/or peptides). The promoter may be heterologous or endogenous.

Multiple elements/promoters may be employed in the context of the present invention to regulate the expression of nucleic acid encoding a fusion protein of the present invention. For example, the promoter/element may be, but is not limited to, lac, pho (e.g. phoA), tac, trc, trp, tet, araBAD, $\lambda P_L$ T3, T7, T7-lac and SP6. Furthermore, it is contemplated that any inducible or constitutively active promoter finds use in the present invention.

Initiation Signals and Internal Ribosome Binding Sites.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

Multiple Cloning Sites.

Vectors may include a multiple cloning site (MCS), which is a nucleic acid region that contains multiple restriction enzyme sites, any of which can be used in conjunction with standard recombinant technology to digest the vector. (See, e.g., Example 1, and Carbonelli et al., 1999, Levenson et al., 1998, and Cocea, 1997, incorporated herein by reference.). "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant nucleic acid technology.

Splicing Sites.

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression.

Polyadenylation Signals.

In expression, a polyadenylation signal may be included to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

Origins of Replication.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

Selectable and Screenable Markers.

In certain embodiments of the invention, in addition to the portion of the fusion protein, and nucleic acid sequences encoding the same, that contains a marker protein, a cell that contains a fusion protein nucleic acid construct of the present invention may be identified in vitro or in vivo by including a marker (e.g., either the same or different marker than that present in the fusion protein) in the expression vector. Such markers confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

The inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a fusion protein of the present invention. Further examples of selectable and screenable markers are well known to one of skill in the art.

With regard to the expression of fusion proteins of the present invention, once a suitable fusion protein nucleic acid encoding sequence has been obtained, one may proceed to prepare an expression system (e.g., expressing fusion protein constructs within host cells). The engineering of DNA segment(s) for expression in a prokaryotic or eukaryotic system may be performed by techniques generally known to those of skill in recombinant expression.

It is believed that virtually any expression system may be employed in the expression of the proteins of the present invention. Prokaryote- and/or eukaryote-based systems can be employed for use with the present invention to produce nucleic acid sequences, or their cognate polypeptides, proteins and peptides. Many such systems are commercially and widely available.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude or more larger than the cDNA gene. However, it is contemplated that a genomic version of a particular gene may be employed where desired.

It is contemplated that a fusion protein of the present invention (e.g., comprising a Tat leader sequence, a target protein and a marker protein) may be co-expressed with other selected proteins, polypeptides or peptides (e.g., protein chaperones, binding partners, and the like, or mutant forms thereof), wherein the proteins are co-expressed in the same cell or gene(s) may be provided to a cell that already has another selected protein. Co-expression may be achieved by co-transfecting the cell with two distinct recombinant vectors, each bearing a copy of either of the respective DNA. Alternatively, a single recombinant vector may be constructed to include the coding regions for each of the proteins of interest (e.g., a fusion protein and a chaperone) that can then be expressed in cells transfected with the single vector. In either event, the term "co-expression" herein refers to the expression of both at least one selected nucleic acid encoding one or more fusion proteins (e.g., comprising at least one or more target proteins) and at least a second selected nucleic acid or gene encoding at least one or more secondary selected proteins, polypeptides or peptides in the same recombinant cell.

In other embodiments, it is contemplated that fusion protein constructs of the present invention can be utilized to identify host cells that are better, or worse, at Tat transport efficiency (See, e.g., Example 6). For example, host cells comprising various chaperone proteins (e.g., co-expressed as described in the preceding paragraph) or mutant chaperone proteins (See Example 6) can be used to determine the role that chaperone proteins (e.g., cytoplasmic chaperone proteins) play in Tat transport and/or target protein solubility.

In some embodiments, the present invention provides a high-throughput screen for monitoring target protein folding and solubility using phage display (See Example 8).

It is contemplated that proteins may be expressed in cell systems or grown in media that enhance protein production. One such system is described in U.S. Pat. No. 5,834,249, incorporated herein by reference in its entirety. In certain embodiments, the fusion protein may be co-expressed with one or more proteins that enhance refolding. Such proteins that enhance refolding include, for example, DsbA or DsbC proteins. A cell system co-expressing the DsbA or DsbC proteins are described in U.S. Pat. No. 5,639,635, incorporated herein by reference in its entirety. In certain embodiments, it is contemplated that a temperature sensitive expression vector may be used to aid assaying protein folding at lower or higher temperatures than many $E.\ coli$ cell strain's optimum growth at about 37° C. For example, a temperature sensitive expression vectors and host cells that express proteins at or below 20° C. is described in U.S. Pat. Nos. 5,654,169 and 5,726,039, each incorporated herein by reference in their entireties.

As used herein, the terms "engineered" and "recombinant" cells or host cells are intended to refer to a cell into which an exogenous DNA segment or gene, such as a cDNA or gene encoding at least one fusion protein has been introduced. Therefore, engineered cells are distinguishable from naturally occurring cells which do not contain a recombinantly introduced exogenous DNA segment or gene. Engineered cells are thus cells having a gene or genes introduced through human intervention. Recombinant cells include those having an introduced cDNA or genomic gene, and also include genes positioned adjacent to a promoter not naturally associated with the particular introduced gene.

In some embodiments, prokaryotic host cells are $E.\ coli$ strain MC4100, B1LK0, RR1, $E.\ coli$ LE392, $E.\ coli$ B, $E.\ coli$ X 1776 (ATCC No. 31537) as well as $E.\ coli$ W3110 (F-, λ-, prototrophic, ATCC No. 273325); bacilli such as *Bacillus subtilis*; and other enterobacteriaceae such as *Salmonella typhimurium*, *Serratia marcescens*, and various *Pseudomonas* species. However, potential host cells are not limited to these examples. Indeed, a host cell may be any species of bacteria selected from the group consisting of *Acetobacter, Actinomyces, Aerobacter, Agribacterium, Azotobacter, Bacillus, Bacteroides, Bordetella, Brucella, Chlamydia, Clostridium, Corynebacterium, Erysipelothrix, Escherichia, Francisella, Fusobacterium, Haemophilus, Klebsiella, Lactobacillus, Listeria, Mycobacterium, Myxococcus, Neisseria, Nocardia, Pasteurella, Proteus, Pseudomonas, Rhizobium, Rickettsia, Salmonella, Serratia, Shigella, Spirilla, Spirillum, Staphylococcus, Streptococcus, Streptomyces, Trepanema, Vibrio, Vibrio*, and *Yersinia*.

In general, plasmid vectors containing replicon and control sequences which are derived from species compatible with the host cell are used in connection with the appropriate hosts. The vector ordinarily carries a replication site, as well as marking sequences which are capable of providing phenotypic selection in transformed cells. For example, $E.\ coli$ is often transformed using derivatives of pBR322, a plasmid derived from an $E.\ coli$ species. pBR322 contains genes for ampicillin and tetracycline resistance and thus provides easy means for identifying transformed cells. The pBR plasmid, or other microbial plasmid or phage may also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage λ GEM$^{TM-11}$ may be utilized in making a recombinant phage vector which can be used to transform host cells, such as $E.\ coli$ LE392.

Other useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Promoters commonly used in recombinant DNA construction include the α-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

In preferred embodiments, recombinant fusion proteins of the present invention are expressed in prokaryotic host cells.

The invention also provides methods for determining the solubility of a target polypeptide. In some embodiments, the present invention provides a method for assessing protein solubility and/or folding comprising providing a nucleic acid encoding a fusion protein comprising a Tat leader signal, a target protein, and a marker protein; expressing the fusion protein in host cells (e.g., bacterial cells); and correlating the ability of the host cells to grow in the presence of a selective agent (e.g., ampicillin) with the solubility and/or folding of the target protein. In preferred embodiments, growth of host cells is indicative of a soluble and/or properly folded target protein. In some embodiments, the fusion protein comprises a TorA signal peptide, a target protein, and TEM1 β-lactamase (Bla) (See, e.g., Examples 1 and 2 and FIG. 1A). In some embodiments, the present invention further provides methods for identifying mutations in a cell that alter the solubility of a target protein.

Although the present invention is not limited to any particular mechanism, and the present invention contemplates a variety of mechanisms, it is believed that, in some embodiments, a target protein that is soluble and/or that folds correctly is exported from the cytoplasm to the periplasm via the Tat pathway and, by virtue of the marker protein (e.g., Bla protein) fusion, confers resistance (e.g., ampicillin resistance) to host cells (e.g., E. coli) expressing the fused marker protein (e.g., the ssTorA-target-Bla chimera). In preferred embodiments, discrimination between folded and misfolded target sequences is accomplished by the Tat machinery such that only correctly folded, soluble proteins are localized to the periplasm. In preferred embodiments, concomitant delivery of a marker protein (e.g., Bla) to the host cell (e.g., E. coli) periplasm confers a resistant phenotype (e.g., ampicillin resistant phenotype) to cells. In some embodiments, growth of host cells correlates with the target protein being soluble and/or properly folded. In some embodiments, a target protein that is not soluble and/or that does not fold correctly is not exported from the cytoplasm to the periplasm via the Tat pathway and therefore does not confer resistance (e.g., ampicillin resistance) to host cells (e.g., E. coli) expressing the fusion protein (e.g., the ssTorA-target-Bla chimera). Thus, in some embodiments, lack of growth of host cells correlates with the target protein being insoluble or not properly folded. In some embodiments, the relative growth rate correlates with the relative periplasmic expression of marker protein (e.g., Bla) activity (i.e., with the solubility of the target protein, See, e.g., Example 3, FIG. 3b). In some embodiments, the methods of the present invention detect intermediate ranges of solubility. (See, e.g., Example 3, FIGS. 2A and 3A).

While it is conceivable that a fusion protein may be delivered directly, a preferred embodiment involves providing a nucleic acid encoding a fusion protein of the present invention to a cell. Following this provision, the fusion protein is synthesized by the transcriptional and translational machinery of the cell. In some embodiments, additional components useful for transcription or translation may be provided by the expression construct comprising fusion protein nucleic acid sequence.

In some embodiments, the nucleic acid encoding the fusion protein may be stably integrated into the genome of the cell. In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on, among other things, the type of expression construct employed.

The ability of certain viruses to infect cells or enter cells via receptor-mediated endocytosis, and to integrate into host cell genome and express viral genes stably and efficiently have made them attractive candidates for the transfer of foreign genes into mammalian cells. In some embodiments, vectors of the present invention are viral vectors (e.g., phage or andenovirus vectors).

Although some viruses that can accept foreign genetic material are limited in the number of nucleotides they can accommodate and in the range of cells they infect, these viruses have been demonstrated to successfully effect gene expression. However, adenoviruses do not integrate their genetic material into the host genome and therefore do not require host replication for gene expression, making them ideally suited for rapid, efficient, heterologous gene expression. Techniques for preparing replication-defective infective viruses are well known in the art.

Of course, in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

A particular method for delivery of the expression constructs involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein.

The expression vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb (See Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP (located at 16.8 map units (m.u.)) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (E1A and E1B; Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). Recently, adenoviral vectors comprising deletions in the E4 region have been described (U.S. Pat. No. 5,670,488, incorporated herein by reference).

In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical adenovirus vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recombinant adenovirus and adeno-associated virus (see below) can both infect and transduce non-dividing human primary cells.

Adeno-associated virus (AAV) is an attractive vector system for use in the cell transduction of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. No. 5,139,941 and U.S. Pat. No. 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Kaplitt et al., 1994; Lebkowski et al., 1988; Samulski et al., 1989; Yoder et al., 1994; Zhou et al., 1994; Hermonat and Muzyczka, 1984; Tratschin et al., 1985; McLaughlin et al., 1988) and genes involved in human diseases (Flotte et al., 1992; Luo et al., 1994; Ohi et al., 1990; Walsh et al., 1994; Wei et al., 1994). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994; Clark et al., 1995). Cell lines carrying the rAAV DNA as an integrated provirus can also be used (Flotte et al., 1995).

Retroviruses have promise as gene delivery vectors due to their ability to integrate their genes into the host genome, transferring a large amount of foreign genetic material, infecting a broad spectrum of species and cell types and of being packaged in special cell-lines (Miller, 1992).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Gene delivery using second generation retroviral vectors has been reported. Kasahara et al. (1994) prepared an engineered variant of the Moloney murine leukemia virus, that normally infects only mouse cells, and modified an envelope protein so that the virus specifically bound to, and infected, human cells bearing the erythropoietin (EPO) receptor. This was achieved by inserting a portion of the EPO sequence into an envelope protein to create a chimeric protein with a new binding specificity.

Other viral vectors may be employed as expression constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In certain further embodiments, the vector will be HSV. A factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations. HSV also is relatively easy to manipulate and can be grown to high titers. Thus, delivery is less of a problem, both in terms of volumes needed to attain sufficient MOI and in a lessened need for repeat dosings.

In still further embodiments of the present invention, the nucleic acids to be delivered are housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

In various embodiments of the invention, nucleic acid sequence encoding a fusion protein is delivered to a cell as an expression construct. In order to effect expression of a gene construct, the expression construct must be delivered into a cell. As described herein, one mechanism for delivery is via viral infection, where the expression construct is encapsidated in an infectious viral particle. However, several non-viral methods for the transfer of expression constructs into cells also are contemplated by the present invention. In one embodiment of the present invention, the expression construct may consist only of naked recombinant DNA or plasmids (e.g., vectors comprising nucleic acid sequences of the present invention). Transfer of the construct may be performed by any of the methods mentioned which physically or chemically permeabilize the cell membrane. Some of these techniques may be successfully adapted for in vivo or ex vivo use, as discussed below.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an expression construct complexed with Lipofectamine (Gibco BRL).

Liposome-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of liposome-mediated delivery and expression of foreign DNA in cultured chick embryo, HeLa and hepatoma cells.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In other embodiments, the delivery vehicle may comprise a ligand and a liposome. Where a bacterial promoter is employed in the DNA construct, it also will be desirable to include within the liposome an appropriate bacterial polymerase.

In certain embodiments of the present invention, the expression construct is introduced into the cell via electroporation. Electroporation involves the exposure of a suspension of cells (e.g., bacterial cells such as E. coli) and DNA to a high-voltage electric discharge.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

In other embodiments of the present invention, the expression construct is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells have been transfected with a neomycin marker gene (Chen and Okayama, 1987), and rat hepatocytes were transfected with a variety of marker genes (Rippe et al., 1990).

In another embodiment, the expression construct is delivered into the cell using DEAE-dextran followed by polyethylene glycol. In this manner, reporter plasmids were introduced into mouse myeloma and erythroleukemia cells (Gopal, 1985).

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Further embodiments of the present invention include the introduction of the expression construct by direct microinjection or sonication loading. Direct microinjection has been used to introduce nucleic acid constructs into Xenopus oocytes (Harland and Weintraub, 1985), and LTK⁻ fibroblasts have been transfected with the thymidine kinase gene by sonication loading (Fechheimer et al., 1987).

In certain embodiments of the present invention, the expression construct is introduced into the cell using adenovirus assisted transfection. Increased transfection efficiencies have been reported in cell systems using adenovirus coupled systems (Kelleher and Vos, 1994; Cotten et al., 1992; Curiel, 1994).

Still further expression constructs that may be employed to deliver nucleic acid construct to target cells are receptor-mediated delivery vehicles. These take advantage of the selective uptake of macromolecules by receptor-mediated endocytosis that will be occurring in the target cells. In view of the cell type-specific distribution of various receptors, this delivery method adds another degree of specificity to the present invention.

Certain receptor-mediated gene targeting vehicles comprise a cell receptor-specific ligand and a DNA-binding agent. Others comprise a cell receptor-specific ligand to which the DNA construct to be delivered has been operatively attached. Several ligands have been used for receptor-mediated gene transfer (Wu and Wu, 1987; Wagner et al., 1990; Perales et al., 1994; Myers, E P O 0273085), which establishes the operability of the technique. In certain aspects of the present invention, the ligand will be chosen to correspond to a receptor specifically expressed on the EOE target cell population.

In other embodiments, the DNA delivery vehicle component of a cell-specific gene targeting vehicle may comprise a specific binding ligand in combination with a liposome. The nucleic acids to be delivered are housed within the liposome and the specific binding ligand is functionally incorporated into the liposome membrane. The liposome will thus specifically bind to the receptors of the target cell and deliver the contents to the cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the DNA delivery vehicle component of the targeted delivery vehicles may be a liposome itself, which will preferably comprise one or more lipids or glycoproteins that direct cell-specific binding. For example, Nicolau et al. (1987) employed lactosyl-ceramide, a galactose-terminal asialganglioside, incorporated into liposomes and observed an increase in the uptake of the insulin gene by hepatocytes. It is contemplated that the tissue-specific transforming constructs of the present invention can be specifically delivered into the target cells in a similar manner.

Homologous recombination (Koller and Smithies, 1992) allows the precise modification of existing genes, overcomes the problems of positional effects and insertional inactivation, and allows the inactivation of specific genes, as well as the replacement of one gene for another. Methods for homologous recombination are described in U.S. Pat. No. 5,614,396, incorporated herein in its entirety by reference.

Thus a preferred method for the delivery of constructs (e.g., comprising nucleic acid encoding a fusion protein of the present invention) involves the use of homologous recombination. Homologous recombination relies, like antisense, on the tendency of nucleic acids to base pair with complementary sequences. In this instance, the base pairing serves to facilitate the interaction of two separate nucleic acid molecules so that strand breakage and repair can take place. In other words, the "homologous" aspect of the method relies on sequence homology to bring two complementary sequences into close proximity, while the "recombination" aspect provides for one complementary sequence to replace the other by virtue of the breaking of certain bonds and the formation of others.

Put into practice, homologous recombination is used generally as follows. First, a site for integration is selected within the host cell. Sequences homologous to the integration site are then included in a genetic construct, flanking the selected gene to be integrated into the genome. Flanking, in this context, simply means that target homologous sequences are located both upstream (5') and downstream (3') of the selected gene. These sequences should correspond to some sequences upstream and downstream of the target gene. The construct is then introduced into the cell, thus permitting recombination between the cellular sequences and the construct.

As a practical matter, the genetic construct will normally act as far more than a vehicle to insert the gene into the genome. For example, it is important to be able to select for recombinants and, therefore, it is common to include within the construct a selectable marker gene. This gene permits selection of cells that have integrated the construct into their genomic DNA by conferring resistance to various biostatic and biocidal drugs. In addition, this technique may be used to "knock-out" (delete) or interrupt a particular gene. Thus, another approach for altering or mutating a gene involves the use of homologous recombination, or "knock-out technology". This is accomplished by including a mutated or vastly deleted form of the heterologous gene between the flanking regions within the construct. The arrangement of a construct to effect homologous recombination might be as follows:

Vector 5'-flanking sequence . . . Tat leader . . . target protein . . . marker protein . . . flanking sequence-3' vector.

Thus, using this kind of construct, it is possible, in a single recombinatorial event, to (i) "knock out" an endogenous gene, (ii) provide a selectable marker for identifying such an event and (iii) introduce a transgene (e.g., nucleic acid encoding a fusion protein of the present invention) for expression Another refinement of the homologous recombination approach involves the use of a "negative" selectable marker. One example is the use of the cytosine deaminase gene in a negative selection method as described in U.S. Pat. No. 5,624,830. The negative selection marker, unlike the selectable marker, causes death of cells which express the marker. Thus, it is used to identify undesirable recombination events. When seeking to select homologous recombinants using a selectable marker, it is difficult in the initial screening step to identify proper homologous recombinants from recombinants generated from random, non-sequence specific events. These recombinants also may contain the selectable marker gene and may express the heterologous protein of interest, but will, in all likelihood, not have the desired phenotype. By attaching a negative selectable marker to the construct, but outside of the flanking regions, one can select against many random recombination events that will incorporate the negative selectable marker. Homologous recombination should not introduce the negative selectable marker, as it is outside of the flanking sequences.

Compositions and methods of the present invention also find use in the discovery of drugs that modulate the solubility and/or folding of proteins (e.g., disease related proteins). For example, the search for pharmaceuticals has focused on the identification of compounds that inhibit cellular processes. However, the increasing prevalence of diseases associated with protein misfolding such as Huntington's disease, Alzheimer's disease, Parkinson's disease, cystic fibrosis, amyotropic lateral schlerosis, Creutzfeld-Jacob disease, and some forms of diabetes and cancer presents a new challenge for the pharmaceutical industry. Thus, the present invention provides compositions and methods for use in screening and assaying protein folding related to these, and other diseases. For example, using the compositions and methods of the present invention, small molecules or other types of agents (pharmaceutical agents) may be identified that stabilizes the folding of a mutant protein involved in disease (e.g., p53). It will be apparent to those skilled in the art that this, and other, aspects of the present invention are easily amenable to a high-throughput procedure to rapidly screen a large number of alternative small molecules or agents (e.g., from a library of such materials). In some embodiments, these methods provide for the development of automated procedures for screening of the small molecules or agents. Thus, the present invention provides incredible savings in time and resources necessary for analyzing the solubility of proteins and materials (e.g., small molecules or agents) useful for altering the same.

Additionally, the compositions and methods of the present invention may be used to identify small molecules or other types of agents (pharmaceutical agents) that can be used to destabilize protein folding (e.g., cause aggregates). In some embodiments, the present invention provides methods for identifying an antibiotic agent.

For example, in some embodiments, the growth of host cells comprising a fusion protein (e.g., comprising a target protein of interest) contacted with a candidate agent (e.g., a candidate drug, pharmaceutical, small molecule or compound) is compared to growth of host cells comprising the fusion protein that is not contacted with the candidate agent. A decrease in growth of the host cells contacted with the candidate agent is indicative of a candidate agent that inhibits protein folding in the cell. In some embodiments, the growth of the host cells, whether or not a candidate agent (e.g., drug or antibiotic agent) is being tested, is under a selective pressure (e.g., exposed to a drug, antibiotic or other selective means).

As used herein, a "candidate agent" may be any agent that potentially inhibits or enhances protein folding and/or solubility, including, but not limited to, a drug, a pharmaceutical, a small molecule, and an compound. For example, the candidate agent may be a protein or fragment thereof, a small molecule, a chemical, or even a nucleic acid molecule. Using lead compounds to help develop improved compounds is know as "rational drug design" and includes not only comparisons with know inhibitors and enhancers of protein folding/solubility, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, it is possible to generate a three-dimensional structure for a target molecule, or a fragment thereof. This could be accomplished by x-ray crystallography, computer modeling or by a combination of both approaches.

It also is possible to use antibodies to ascertain the structure of a candidate enhancer or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful candidate agents. Screening of such libraries, including combinatorially generated libraries (e.g., peptide libraries), is a rapid and efficient way to screen large number of related (and unrelated) agents for activity. Combinatorial approaches also lend themselves to rapid evolution of potential drugs by the creation of second, third and fourth generation compounds modeled of active, but otherwise undesirable compounds.

Candidate agents may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the agents (e.g., pharmaceuticals) to be screened could also be derived or synthesized from chemical compositions or man-made compounds. Thus, it is understood that the candidate agent identified by the present invention may be any peptide, polypeptide, polynucleotide, small molecule inhibitors or any other chemicals or compounds (e.g., that may be designed through rational drug design starting from known inhibitors or enhancers).

Other potential agents include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating agents (e.g., compounds) initially identified, other sterically similar compounds may be formulated to mimic the key portions of the structure of the modulators. Such agents (e.g., compounds), which may include peptidomimetics of peptide modulators, may be used in the same manner as the initial modulators.

The invention also provides gene delivery vehicles and expression vectors and host or genetically modified cells containing at least polynucleotides of the invention and/or a fusion protein of the invention.

The present invention also provides gene delivery vehicles suitable for delivery and/or expression of a polynucleotide sequence (e.g., a nucleic acid sequence encoding a fusion protein of the present invention) of the invention into cells (whether in vivo, ex vivo, or in vitro). A polynucleotide sequence of the invention can be contained within a cloning or expression vector. These vectors (especially expression vectors) can in turn be manipulated to assume any of a number of forms which may, for example, facilitate delivery to and/or entry into a cell. Examples of suitable expression and delivery vehicles are provided elsewhere herein.

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. In some embodiments, a host cell is used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes. Prokaryotes include gram negative or positive bacterial cells. Numerous cell lines and cultures are available for use as a host cell, and they can be obtained through the American Type Culture Collection (ATCC), an organization that serves as an archive for living cultures and genetic materials (www.atcc.org). An appropriate host can be determined by one of skill in the art based on the vector nucleic acid sequence and the desired result. A plasmid or cosmid, for example, can be introduced into a prokaryote host cell for replication of many vectors. Bacterial cells used as host cells for expression vector replication and/or expression include, among those listed elsewhere herein, DH5α, JM109, and KC8, as well as a number of commercially available bacterial hosts such as SURE™ Competent Cells and SOLOPACK™ Gold Cells (Stratagene, La Jolla). Alternatively, bacterial cells such as *E. coli* LE392 can be used as host cells for phage viruses.

Examples of eukaryotic host cells for replication and/or expression of a vector include *C. elegans*, HeLa, NIH3T3, Jurkat, 293, Cos, CHO, Saos, yeast, nematodes, insect cells, and PC12. Many host cells from various cell types and organisms are available and are known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector and/or expression of nucleic acid sequences present within the vector. Also understood and known are techniques and conditions that allow large-scale production of vectors, as well as production of the nucleic acids encoded by vectors and their cognate polypeptides, proteins, or peptides.

The fusion protein constructs, host cells and methods of the present invention are also useful for identifying variations in a process for biosynthesis of a target protein. The process can be varied to modify the solubility of the target protein. For example, a cell containing a fusion protein nucleic acid is cultured under alternative conditions and the growth of the host cells under selective conditions monitored. For example, protein solubility may be affected by the temperature, medium composition, or oxygen concentration in which the host cells are cultured. The method by which host cell growth is measured provides an immediate readout of solubility and permits a variety of alternative conditions to be tested with minimal effort, to identify those conditions where the highest proportion of soluble target protein is produced.

The constructs also are useful to compare alternative cells to identify a cell that synthesizes an increased amount of soluble target protein by performing a method identified herein with at least two alternative cells and comparing the amount of host cell growth to identify a cell that expresses an increased amount of soluble target protein.

The invention is not limited to any particular host cell. A host cell may be prokaryotic or eukaryotic. Indeed, a variety of host cells are contemplated to be useful in the present invention, including, but not limited to, any species selected from the group consisting of *Acetobacter, Actinomyces, Aerobacter, Agribacterium, Azotobacter, Bacillus, Bacteroides, Bordetella, Brucella, Chlamydia, Clostridium, Corynebacterium, Erysipelothrix, Escherichia, Francisella, Fusobacterium, Haemophilus, Klebsiella, Lactobacillus, Listeria, Mycobacterium, Myxococcus, Neisseria, Nocardia, Pasteurella, Proteus, Pseudomonas, Rhizobium, Rickettsia, Salmonella, Serratia, Shigella, Spirilla, Spirillum, Staphylococcus, Streptococcus, Streptomyces, Trepanema, Vibrio, Vibrio,* and *Yersinia*. In some preferred embodiments, the host cell is *E. coli* strain MC4100 or B1LK0.

The present invention also provides host or genetically modified cells containing the fusion protein constructs of the present invention (See, e.g., Example 1). Arrays of cells are also provided, in which the cells of each population differ in the fusion protein expressed by the cells. For example, the fusion proteins can differ due to amino acid substitutions, deletions, or insertions in the target protein compared to a reference target protein amino acid sequence (e.g., an unmodified or wild type target protein sequence). Alternatively, the target proteins expressed by the populations of host cells can be different fragments of a larger polypeptide.

The invention also provides a method for screening for mutations in a host cell, or in a target protein sequence, that improve the solubility of a target protein. For example, cells comprising a fusion protein of the present invention can be treated with a mutagen, and those host cells that display an increase in growth (e.g., rate or abundance) in the presence of a selective marker (e.g., ampicillin) identified. A "mutagen" is intended to include, but not be limited to chemical mutagens such as ethyl methane sulphonate, N-methyl-N'-nitroso-guanidine and nitrous acid as well as physical agents such as ionizing radiation.

In an alternative embodiment, mutations can be introduced into a polynucleotide sequence encoding a target protein. The altered polynucleotide is then tested to determine whether the solubility of the target protein is changed (e.g., as monitored by growth in a selective environment, e.g., in the presence of ampicillin). Such mutations include, but are not limited to, mutations induced by a mutagen; site directed mutations that alter specific amino acid residues such as mutation of cysteine residues to eliminate disulfide bonds; deletions that remove sets of specific amino acids such as deletion of a continuous stretch of hydrophobic amino acids; and fusions of the target protein to a second, particularly soluble protein. In each case, the solubility of the target protein is assessed by determining growth of the host cells in a selective environment.

Where employed, mutagenesis can be accomplished by a variety of standard, mutagenic procedures. Mutation can involve modification of the nucleotide sequence of a single gene, blocks of genes or whole chromosome. Changes in single genes may be the consequence of point mutations which involve the removal, addition or substitution of a single nucleotide base within a DNA sequence, or they may be the consequence of changes involving the insertion or deletion of large numbers of nucleotides.

Mutations can arise spontaneously as a result of events such as errors in the fidelity of DNA replication or the movement of transposable genetic elements (transposons) within the genome. They also are induced following exposure to chemical or physical mutagens. Such mutation-inducing agents include ionizing radiations, ultraviolet light and a diverse array of chemical such as alkylating agents and polycyclic aromatic hydrocarbons all of which are capable of interacting either directly or indirectly (generally following some metabolic biotransformations) with nucleic acids. The DNA lesions induced by such environmental agents may lead to modifications of base sequence when the affected DNA is replicated or repaired and thus to a mutation. Mutation also can be site-directed through the use of particular targeting methods.

Random Mutagenesis.

i) Insertional Mutagenesis

Insertional mutagenesis is based on the inactivation of a gene via insertion of a known DNA fragment. Because it involves the insertion of some type of nucleic acid (e.g., DNA) fragment, the mutations generated are generally loss-of-function, rather than gain-of-function mutations. However, there are several examples of insertions generating gain-of-function mutations. Insertion mutagenesis has been very successful in bacteria and *Drosophila*.

Transposable genetic elements are DNA sequences that can move (transpose) from one place to another in the genome of a cell. The first transposable elements to be recognized were the Activator/Dissociation elements of *Zea mays*. Since then, they have been identified in a wide range of organisms, both prokaryotic and eukaryotic.

Transposable elements in the genome are characterized by being flanked by direct repeats of a short sequence of DNA that has been duplicated during transposition and is called a target site duplication. Virtually all transposable elements whatever their type, and mechanism of transposition, make such duplications at the site of their insertion. In some cases the number of bases duplicated is constant, in other cases it may vary with each transposition event. Most transposable elements have inverted repeat sequences at their termini. These terminal inverted repeats may be anything from a few bases to a few hundred bases long and in many cases they are known to be necessary for transposition.

Prokaryotic transposable elements have been most studied in *E. coli* and Gram negative bacteria, but also are present in Gram positive bacteria. They are generally termed insertion sequences if they are less than about 2 kB long, or transposons if they are longer. Bacteriophages such as mu and D108, which replicate by transposition, make up a third type of transposable element. elements of each type encode at least one polypeptide a transposase, required for their own transposition. Transposons often further include genes coding for function unrelated to transposition, for example, antibiotic resistance genes.

Transposons can be divided into two classes according to their structure. First, compound or composite transposons have copies of an insertion sequence element at each end, usually in an inverted orientation. These transposons require transposases encoded by one of their terminal IS elements. The second class of transposon have terminal repeats of about 30 base pairs and do not contain sequences from IS elements.

Transposition usually is either conservative or replicative, although in some cases it can be both. In replicative transposition, one copy of the transposing element remains at the donor site, and another is inserted at the target site. In conservative transposition, the transposing element is excised from one site and inserted at another.

Eukaryotic elements also can be classified according to their structure and mechanism of transportation. The primary distinction is between elements that transpose via an RNA intermediate, and elements that transpose directly from DNA to DNA.

Elements that transpose via an RNA intermediate often are referred to as retrotransposons, and their most characteristic feature is that they encode polypeptides that are believed to have reverse transcriptionase activity. There are two types of retrotransposon. Some resemble the integrated proviral DNA of a retrovirus in that they have long direct repeat sequences, long terminal repeats (LTRs), at each end. The similarity between these retrotransposons and proviruses extends to their coding capacity. They contain sequences related to the gag and pol genes of a retrovirus, suggesting that they transpose by a mechanism related to a retroviral life cycle. Retrotransposons of the second type have no terminal repeats. They also code for gag- and pol-like polypeptides and transpose by reverse transcription of RNA intermediates, but do so by a mechanism that differs from that or retrovirus-like elements. Transposition by reverse transcription is a replicative process and does not require excision of an element from a donor site.

Transposable elements are an important source of spontaneous mutations, and have influenced the ways in which genes and genomes have evolved. They can inactivate genes by inserting within them, and can cause gross chromosomal rearrangements either directly, through the activity of their transposases, or indirectly, as a result of recombination between copies of an element scattered around the genome. Transposable elements that excise often do so imprecisely and may produce alleles coding for altered gene products if the number of bases added or deleted is a multiple of three.

Transposable elements themselves may evolve in unusual ways. If they were inherited like other DNA sequences, then copies of an element in one species would be more like copies in closely related species than copies in more distant species. This is not always the case, suggesting that transposable elements are occasionally transmitted horizontally. from one species to another.

ii) Chemical Mutagenesis.

Chemical mutagenesis offers certain advantages, such as the ability to find a full range of mutant alleles with degrees of phenotypic severity, and is facile and inexpensive to perform. The majority of chemical carcinogens produce mutations in DNA. Benzo(a)pyrene, N-acetoxy-2-acetyl aminofluorene and aflotoxin B1 cause GC to TA transversions in bacteria and mammalian cells. Benzo(a)pyrene also can produce base substitutions such as AT to TA. N-nitroso compounds produce GC to AT transitions. Alkylation of the O4 position of thymine induced by exposure to n-nitrosoureas results in TA to CG transitions.

A high correlation between mutagenicity and carcinogenity is the underlying assumption behind the Ames test (McCann et al., 1975) which speedily assays for mutants in a bacterial system, together with an added rat liver homogenate, which contains the microsomal cytochrome P450, to provide the metabolic activation of the mutagens where needed.

In vertebrates, several carcinogens have been found to produce mutation in the ras protooncogene. N-nitroso-N-methyl urea induces mammary, prostate and other carcinomas in rats with the majority of the tumors showing a G to A transition at the second position in codon 12 of the Ha-ras oncogene. Benzo(a)pyrene-induced skin tumors contain A to T transformation in the second codon of the Ha-ras gene.

iii) Radiation Mutagenesis.

The integrity of biological molecules is degraded by the ionizing radiation. Adsorption of the incident energy leads to the formation of ions and free radicals, and breakage of some covalent bonds. Susceptibility to radiation damage appears quite variable between molecules, and between different crystalline forms of the same molecule. It depends on the total accumulated dose, and also on the dose rate (as once free radicals are present, the molecular damage they cause depends on their natural diffusion rate and thus upon real time). Damage is reduced and controlled by making the sample as cold as possible.

Ionizing radiation causes DNA damage and cell killing, generally proportional to the dose rate. Ionizing radiation has been postulated to induce multiple biological effects by direct interaction with DNA, or through the formation of free radical species leading to DNA damage. These effects include gene mutations, malignant transformation, and cell killing. Although ionizing radiation has been demonstrated to induce expression of certain DNA repair genes in some prokaryotic and lower eukaryotic cells, little is known about the effects of ionizing radiation on the regulation of mammalian gene expression (Borek, 1985). Several studies have described changes in the pattern of protein synthesis observed after irradiation of mammalian cells. For example, ionizing radiation treatment of human malignant melanoma cells is associated with induction of several unidentified proteins (Boothman et al., 1989). Synthesis of cyclin and co-regulated polypeptides is suppressed by ionizing radiation in rat REF52 cells, but not in oncogene-transformed REF52 cell lines (Lambert and Borek, 1988). Other studies have demonstrated that certain growth factors or cytokines may be involved in x-ray-induced DNA damage. In this regard, platelet-derived growth factor is released from endothelial cells after irradiation (Witte, et al., 1989).

In the present invention, the term "ionizing radiation" means radiation comprising particles or photons that have sufficient energy or can produce sufficient energy via nuclear interactions to produce ionization (gain or loss of electrons). An exemplary and preferred ionizing radiation is an γ-radiation. The amount of ionizing radiation needed in a given cell generally depends upon the nature of that cell. Typically, an effective expression-inducing dose is less than a dose of ionizing radiation that causes cell damage or death directly. Means for determining an effective amount of radiation are well known in the art.

In a certain embodiments, an effective expression inducing amount is from about 2 to about 30 Gray (Gy) administered at a rate of from about 0.5 to about 2 Gy/minute. Even more preferably, an effective expression inducing amount of ionizing radiation is from about 5 to about 15 Gy. In other embodiments, doses of 2-9 Gy are used in single doses. An effective dose of ionizing radiation may be from 10 to 100 Gy, with 15 to 75 Gy being preferred, and 20 to 50 Gy being more preferred.

Any suitable means for delivering radiation to a tissue may be employed in the present invention in addition to external means. For example, radiation may be delivered by first providing a radiolabeled antibody that immunoreacts with an antigen of the tumor, followed by delivering an effective amount of the radiolabeled antibody to the tumor. In addition, radioisotopes may be used to deliver ionizing radiation to a tissue or cell.

iv) In Vitro Scanning Mutagenesis.

Random mutagenesis also may be introduced (e.g., using error prone PCR, See Cadwell and Joyce, 1992). The rate of mutagenesis may be increased by performing PCR in multiple tubes with dilutions of templates.

One particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation.

In recent years, techniques for estimating the equilibrium constant for ligand binding using minuscule amounts of protein have been developed (See, e.g., U.S. Pat. Nos. 5,221,605 and 5,238,808, herein incorporated by reference in their entireties). The ability to perform functional assays with small amounts of material can be exploited to develop highly efficient, in vitro methodologies for the saturation mutagenesis of antibodies. The inventors bypassed cloning steps by combining PCR mutagenesis with coupled in vitro transcription/translation for the high throughput generation of protein mutants. Here, the PCR products are used directly as the template for the in vitro transcription/translation of the mutant single chain antibodies. Because of the high efficiency with which all 19 amino acid substitutions can be generated and analyzed in this way, it is now possible to perform saturation mutagenesis on numerous residues of interest, a process that can be described as in vitro scanning saturation mutagenesis (Burks et al., 1997).

In vitro scanning saturation mutagenesis provides a rapid method for obtaining a large amount of structure-function information including: (i) identification of residues that modulate ligand binding specificity, (ii) a better understanding of ligand binding based on the identification of those amino acids that retain activity and those that abolish activity at a given location, (iii) an evaluation of the overall plasticity of an active site or protein subdomain, (iv) identification of amino acid substitutions that result in increased binding.

v) Random Mutagenesis by Fragmentation and Reassembly.

A method for generating libraries of displayed polypeptides is described in U.S. Pat. No. 5,380,721, herein incorporated by reference in its entirety. The method comprises obtaining polynucleotide library members, pooling and fragmenting the polynucleotides, and reforming fragments therefrom, performing PCR amplification, thereby homologously recombining the fragments to form a shuffled pool of recombined polynucleotides.

b. Site-Directed Mutagenesis

Structure-guided site-specific mutagenesis represents a powerful tool for the dissection and engineering of protein-ligand interactions. The technique provides for the preparation and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. For example, a primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as *E. coli* polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as *E. coli* cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multiresidue saturation mutagenesis are daunting (Warren et al., 1996, Zeng et al., 1996; Yelton et al., 1995; Hilton et al., 1996). Hundreds, and possibly even thousands, of site specific mutants must be studied. However, improved techniques make production and rapid screening of mutants much more straightforward. See, U.S. Pat. Nos. 5,798,208 and 5,830,650, herein incorporated by reference in their entireties, for a description of "walk-through" mutagenesis.

Other methods of site-directed mutagenesis are disclosed in U.S. Pat. Nos. 5,220,007; 5,284,760; 5,354,670; 5,366,878; 5,389,514; 5,635,377; and 5,789,166, herein incorporated by reference in their entireties.

In some embodiments, a variant (e.g., a mutant) includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

vi. Directed Evolution.

In some embodiments, variants may be produced by methods such as directed evolution or other techniques for producing combinatorial libraries of variants. The synthesis of degenerate oligonucleotides is well known in the art (See e.g., Narang, Tetrahedron Lett., 39:39 (1983); Itakura et al., Recombinant DNA, in Walton (ed.), Proceedings of the 3rd Cleveland Symposium on Macromolecules, Elsevier, Amsterdam, pp 273-289 (1981); Itakura et al., Annu. Rev. Biochem., 53:323 (1984); Itakura et al., Science 198:1056 (1984); Ike et al., Nucl. Acid Res., 11:477 (1983), herein incorporated by reference in their entireties). Such techniques have been employed in the directed evolution of proteins (See e.g., Scott et al., Science 249:386 (1980); Roberts et al., Proc. Natl. Acad. Sci. USA 89:2429 (1992); Devlin et al., Science 249: 404 (1990); Cwirla et al., Proc. Natl. Acad. Sci. USA 87: 6378 (1990); each of which is herein incorporated by reference; as well as U.S. Pat. Nos. 5,223,409, 5,198,346, and 5,096,815; each of which is incorporated herein by reference).

The present invention also provides methods for screening an expression library of clones to identify those clones that express soluble protein. This library can consist of alterations in the gene (or portion thereof) expressing the target protein (or portion thereof) of interest. Alterations of the gene can be provided by any of several widely used methods. These include, but are not limited to, making truncations in the gene, random chemical mutagenesis, random mutagenesis through erroneous nucleotide incorporation, or site-directed mutagenesis methods. This library of alterations can then be transformed into host cells. Individual clones of the transformed host cells are then cultured under conditions where the fusion protein containing a target protein, or altered form thereof, are expressed. The growth of the host cells in a selective environment (e.g., in the presence of ampicillin) can then be measured. Thus, host cell clones that are able to grow or that display increased growth (e.g., rate of growth) are identified that contain more soluble derivatives of the target protein. Likewise, if desired, clones that contain a less soluble form of the target protein can also be identified in host cell clones that fail to grow or that grow more slowly.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: g (grams); l or L (liters); μg (micrograms); μl (microliters); μm (micrometers); μM (micromolar); μmol (micromoles); mg (milligrams); ml (milliliters); mm (millimeters); mM (millimolar); mmol (millimoles); M (molar); mol (moles); ng (nanograms); nm (nanometers); nmol (nanomoles); N (normal); pmol (picomoles); Sigma (Sigma Chemical Co., St. Louis, Mo.); Amersham (Amersham, GE Health, Piscataway, N.J.); BioTek (Bio-Tek Instruments, Inc., Winooski, Vt.); Clontech (BD Biosciences Clontech, Mountain View, Calif.); Abcam (Abcam, Inc., Cambridge, Mass.).

Example 1

Materials and Methods

Bacterial strains and plasmids. Wildtype *E. coli* strain MC4100 and a ΔtatC derivative of MC4100, strain B1LK0 (See, e.g., Bogsch et al., J Biol Chem 273, 18003-18006 (1998)), were used for all experiments. Plasmids for cytoplasmic expression of MBP (wt) and its folding mutant derivatives (See, e.g., Betton and Hofnung, J Biol Chem 271, 8046-8052 (1996)) were generated by inserting the gene encoding each MBP sequence into the NcoI/HindIII position of pTrc99A (Amersham Pharmacia). Plasmids for expressing MBP and its derivatives via the Tat pathway were created by excising the phoA gene from pTorA-AP (See, e.g., DeLisa et al., Proc Natl Acad Sci USA 100, 6115-6120 (2003)) with XbaI and HindIII and inserting the gene encoding mature MBP (wt) or a folding mutant into the resulting XbaI/HindIII sites. Similarly, plasmids for localizing DsRed and its derivatives to the Tat pathway were generated by inserting either the DsRed gene sequence or its derivatives, dimer2 and mRFP1 (See, e.g., Campbell et al., Proc Natl Acad Sci USA 99, 7877-7882 (2002)), into XbaI/HindIII-digested pTorA-AP.

All folding reporter plasmids generated in this study were derivatives of pTrc99A which was previously modified by replacing the β-lactamase (Bla) gene with a $Cm^r$ cassette to generate pTrc99A-Cm. To generate the folding reporter plasmids, plasmid pTorA-cassette-Cm was first constructed by inserting a cDNA encoding the complete amino acid sequence (amino acids 1-46) of the *E. coli* Tat-dependent TorA signal peptide (ssTorA) plus the first eight residues of mature TorA (See, e.g., DeLisa et al., J Biol Chem 277, 29825-29831 (2002)) into pTrc99A-Cm between NcoI and EcoRI. Next, the Bla gene was amplified from pTrc99A and cloned into plasmid pTorA-cassette between XbaI and HindIII. The forward primer for the Bla gene included 2 additional restriction sites (BamHI and SalI) immediately after XbaI to create a mini-MCS between ssTorA and Bla. The resulting plasmid was named pTMB and was used for generating folding reporter plasmids. In general, a target gene was cloned with XbaI and SalI restriction sites at the 5' and 3' ends, respectively, allowing for directional cloning of the target gene into the same sites of pTMB. All plasmids constructed in this study were confirmed by DNA sequencing.

Cell growth assays. For monitoring the folding and solubility of target sequences, cells carrying a folding reporter plasmid were grown overnight in LB medium containing chloramphenicol (25 μg/mL). Screening of cells on solid plates was performed by spotting 5 μL of an equivalent number of cells directly onto LB agar plates supplemented with ampicillin (100 μg/mL) or chloramphenicol (25 μg/mL) and growing overnight at 25° C. Screening of cells in liquid culture was performed by inoculating 10 μL of overnight cells into 100 μL of LB plus ampicillin (100 μg/mL) in a 96-well plate. Cells were grown with aeration at 37° C. for 6 hours and the cell growth rate was monitored by measuring the change in absorbance at 595 nm using a plate reader (BioTek SynergyHT plate reader).

Subcellular fractionations. For all fractionation experiments, an equivalent number of cells were harvested following 6 hours of growth in liquid culture, pelleted by centrifugation and fractionated by the ice-cold osmotic shock procedure (See, e.g., Bogsch et al., J Biol Chem 273, 18003-18006 (1998)). Specifically, an equivalent number of cells were collected by centrifugation and resuspended in a buffer containing 100 mM Tris-Cl (pH 8.0), 0.5M sucrose, and 1 mM NaEDTA. Cells were incubated for 10 min at room temperature and then centrifuged. Next, the buffer was decanted and the pellet was resuspended in 266 μL ice-cold 5 mM $MgSO_4$ and placed on ice for an additional 10 min. Following centrifugation, the supernatant containing periplasmic proteins was collected for electrophoretic analysis. The pellet containing the cytoplasmic fraction was resuspended in 266 µl of PBS and homogenized by sonification. Homogenized cells were centrifuged and the supernatant was collected as the cytoplasmic fraction.

Western blot analysis. Western blotting was performed as previously described (DeLisa et al., Proc Natl Acad Sci USA 100, 6115-6120 (2003)). All lanes of SDS-12% polyacrylamide gels were loaded with samples prepared from an equivalent number of cells harvested from each experiment. The following primary antibodies were used: monoclonal mouse anti-MBP (Sigma) diluted 1:2,000; monoclonal anti-DsRed (Clontech) diluted 1:2,000; monoclonal mouse anti-beta-lactamase (Abcam) diluted 1:2,000 and polyclonal rabbit anti-GroEL (Sigma) diluted 1:20,000. The secondary antibody was 1:2,000 goat anti-mouse and goat anti-rabbit horseradish peroxidase. Membranes were first probed with anti-polyhistidine antibody and, following development, were stripped in Tris-buffered saline/2% SDS/0.7 M β-mercaptoethanol. Stripped membranes were re-blocked and probed with anti-GroEL antibody.

β-lactamase activity assay. Subcellular fractions were assayed for α-lactamase activity in 96-well format. Briefly, 20 µl of a periplasmic or cytoplasmic sample was assayed for hydrolysis of nitrocefin (50 µM) by monitoring the increase in absorbance at 490 nm in 100 mM sodium phosphate buffer (pH 7.0).

Example 2

Folding Quality Control of the Tat Pathway

Figure 2:
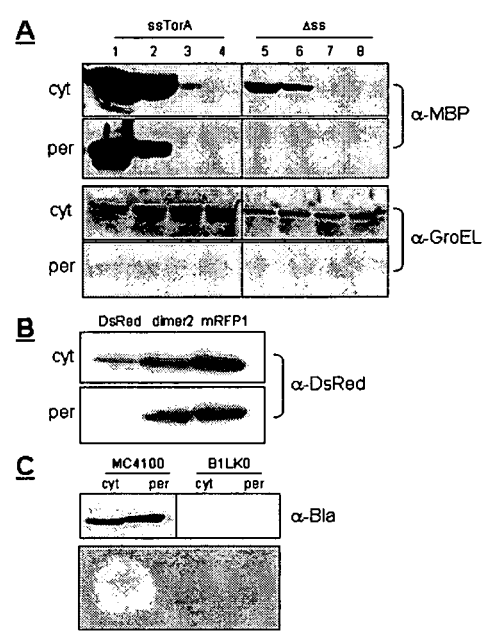
FIG. 2 depicts the proofreading of misfolded proteins by the Tat system. (A) Subcellular distribution of: (1) MBP (wt); (2) MBP (G32D); (3) MBP (I33P); and (4) MalE31 (MBP G32D/I33P) expressed via the Tat pathway (ssTorA) or in the cytoplasm (Δss) probed by anti-MBP antiserum. GroEL was used as a fractionation marker by probing with anti-GroEL serum. (B) Subcellular distribution of: ssTorA-DsRed, ssTorA-dimer2 and ssTorA-mRFP1 probed by anti-DsRed antiserum. (C) Subcellular distribution of ssTorA-Bla in MC4100 and B1LK0 (as MC4100 ΔtatC) cells carrying pTMB determined by anti-DsRed antiserum and growth of MC4100/pTMB and B1LK0/pTMB cells on LB agar plates supplemented with 100 μg/mL ampicillin.

Tat transport of *E. coli* maltose binding protein (MBP) and three well-characterized MBP mutants prone to varying levels of off-pathway folding intermediates: MBP-G32D, MBP-I33P, and MalE31 (G32D/I33P) (See, e.g., Betton and Hofnung, J Biol Chem 271, 8046-8052 (1996)) was evaluated. These proteins display a >100-fold difference in in vivo solubility with unfolding/refolding stability ranging from −5.5 kcal/mol to −9.5 kcal/mol ((See, e.g., Betton and Hofnung, J Biol Chem 271, 8046-8052 (1996)). The coding region for the well-characterized *E. coli* TMAO reductase twin-arginine signal peptide plus the first 4 residues of mature TorA (ssTorA, amino acids 1-46) (DeLisa et al., J Biol Chem 277, 29825-29831 (2002)) was fused upstream of the gene encoding the mature form of each MBP (residues 26-396), thus creating four ssTorA-MBP chimeras. Cell fractionation of wildtype MC4100 *E. coli* cells was performed to track subcellular localization and revealed that the periplasmic yield of each MBP mutant was consistent with the level of soluble expression in the cytoplasm (FIG. 2A). Importantly, no transport of any of the MBP proteins was observed in a ΔtatC mutant of MC4100 (strain B1LK0) (See, e.g., Bogsch et al., J Biol Chem 273, 18003-18006 (1998)) that is incapable of Tat transport, confirming that this was a Tat-specific phenomenon.

To further test the generality of the quality control mechanism, the non-endogenous *Discosoma* coral DsRed and two well-characterized mutants derived from DsRed, namely dimer2 and mRFP1 (See, e.g., Campbell et al., Proc Natl Acad Sci USA 99, 7877-7882 (2002)) was examined. Whereas DsRed forms obligate tetramers with a tendency toward intracellular aggregation, Tsien and coworkers successfully evolved a tandem dimer of DsRed (dimer2), with fewer proclivities to aggregate, and a monomeric variant (mRFP1), which does not aggregate in vivo. As above, by fusing the coding region of the TorA signal peptide upstream of the DsRed gene it was possible to construct three ssTorA-DsRed chimeras and track subcellular localization. The periplasmic yield of each fusion protein in MC4100 cells was consistent with the level of soluble expression in the cytoplasm (FIG. 2B) whereas no transport was observed for any of the three fusion proteins in B1LK0 cells. Taken together, the present invention demonstrates that by regulating export to the periplasmic space, the quality control mechanism of the Tat system is generally robust in sensing ratiometric changes in heterologous substrate solubility.

Example 3

Tat-Based Solubility Reporter

To exploit the quality control feature of the Tat pathway for monitoring protein solubility, a genetic assay that employs a tripartite fusion of the TorA signal peptide, a 'target' protein, and mature TEM1 β-lactamase (Bla) (FIG. 1A) was developed. The premise for this assay is as follows: a soluble target protein is exported to the periplasm via the Tat pathway and, by virtue of the Bla fusion, confers ampicillin resistance to *E. coli* cells expressing the ssTorA-target-Bla chimera. To verify that Bla is indeed capable of reporting Tat dependent transport in the assay, a vector (pTMB, FIG. 1B) was first constructed with no gene in the target position that expresses ssTorA-Bla. Upon expression of ssTorA-Bla in MC4100 and B1LK0, only periplasmic Bla localization was observed with a corresponding ampicillin resistance phenotype in MC4100 cells that possess a functional Tat pathway (FIG. 2C). Thus, Bla can be specifically transported by the Tat pathway.

Figure 3:
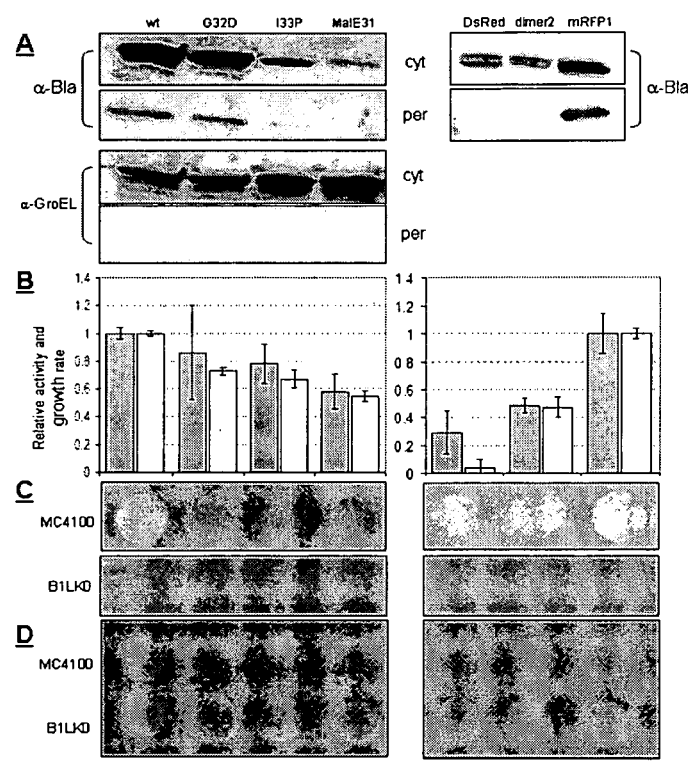
FIG. 3 shows cell growth on ampicillin correlates with solubility of target protein. Cytoplasmic (cyt) and periplasmic (per) fractions are shown. Cells expressing ssTorA-MBP (wt)-Bla, ssTorA-MBP(G32D)-Bla, ssTorA-MBP(I33P)-Bla, and ssTorA-MalE31-Bla (left panel) and ssTorA-DsRed-Bla, ssTorA-dimer2-Bla and ssTorA-mRFP1-Bla were assayed for: (A) subcellular distribution of the fusion protein by probing with anti-β-lactamase antiserum (left panel) and anti-DsRed antiserum (right panel). GroEL was used as a fractionation marker by probing with anti-GroEL serum.

Next, the gene encoding mature MBP or one of the three mutants (G32D, I33P, and MalE31) was inserted into the target position of pTMB. Upon expression in MC4100, it was found that the amount of soluble ssTorA-MBP-Bla fusion protein in the cytoplasm correlated both to the periplasmic yield of the fusion protein and the growth rate in the presence of ampicillin (FIGS. 3A and B). In addition, the varying relative growth rate agreed well with the relative periplasmic Bla activity (FIG. 3B). Furthermore, it is possible to effectively report intermediate changes in target protein solubility. Indeed, the differences in MBP solubility reported by the assay of the present invention were in agreement with the solubility of MBP expressed both with and without a signal peptide (compare FIGS. 2A and 3A), as well as with previous reports of wildtype and variant MBP solubility in the *E. coli* cytoplasm (See, e.g., Wigley et al., Nat Biotechnol 19, 131-136 (2001); Betton and Hofnung, J Biol Chem 271, 8046-8052 (1996)). It should be noted that growth on solid medium containing antibiotics could be used to discriminate between cells expressing soluble MBP versus an insoluble variant (FIG. 3C). As no growth was observed for B1LK0 cells on ampicillin expressing any of the ssTorA-MBP-Bla fusions, it is possible that the fusions are exclusively routed via the Tat pathway. Importantly, B1LK0 cells carrying reporter plasmids grew equally well as wildtype MC4100 in the absence of ampicillin (FIG. 3D) confirming that lack of growth of B1LK0 cells on ampicillin was due to a blockage in transport and not due to a growth defect of the cells.

In addition, plasmids were constructed encoding the DsRed, dimer2, and mRFP1 gene sequences inserted as targets in pTMB. Cells expressing ssTorA-DsRed-Bla did not localize the fusion protein to the periplasm and were incapable of growth on ampicillin (FIGS. 3A, B and C), consistent with our earlier observation that DsRed alone is not transported via the Tat mechanism. On the other hand, cells expressing ssTorA-mRFP1-Bla showed significant periplasmic accumulation of the fusion protein and were resistant to ampicillin, both strong indicators of the monomerization and increased solubility of mRFP1 relative to wildtype DsRed (FIGS. 3A, B and C). There was virtually no ssTorA-dimer2-Bla fusion detected in the periplasm as evidenced by Western blotting (FIG. 3A, right panel, lane 2), however, cells expressing this fusion displayed intermediate levels of periplasmic Bla activity and growth on ampicillin which were significantly above those seen for cells expressing DsRed fusions (FIGS. 3B and C). This intermediate level of Bla transport coincided directly with the quantity of periplasmic ssTorA-dimer2 expressed in the absence of a C-terminal Bla fusion partner. Finally, no growth was observed for B1LK0 cells expressing any of the ssTorA-DsRed-Bla fusions indicating that transport is Tat-specific.

Figure 4:
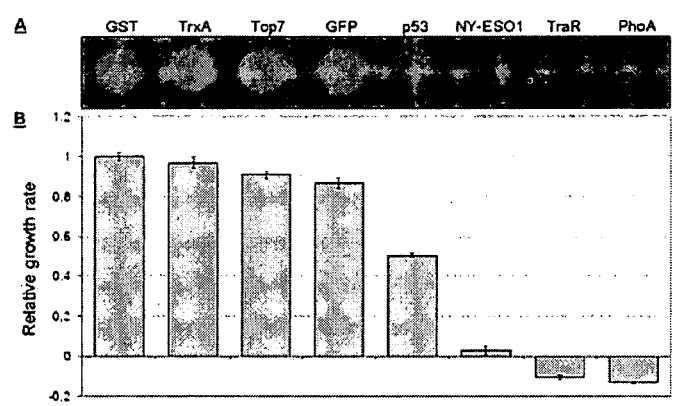
FIG. 4 shows a broad spectrum of target proteins are correctly reported by Tat-specific genetic selection-based assays.

To explore the generality of this assay, 8 additional test proteins of prokaryotic and eukaryotic origin were cloned into the target position of our folding reporter. These target proteins ranged from the highly soluble *E. coli* proteins thioredoxin (TrxA) and glutathione S-transferase (GST) to *E. coli* alkaline phosphatase (PhoA), a periplasmic enzyme that is not able to fold in the cytoplasm due to the presence of two disulfide bonds in its native structure (See, e.g., Sone et al., J Biol Chem 272, 6174-6178 (1997)) and TraR, a transcriptional activator from *Agrobacterium tumefaciens* that is highly unstable in the *E. coli* cytoplasm when expressed in the absence of its cognate autoinducer (See, e.g., Zhu and Winans, Proc Natl Acad Sci USA 98, 1507-1512 (2001)). Remarkably, expression of all target proteins that were known to be soluble in the cytoplasm, namely TrxA, GST, green fluorescent protein (GFP), Top7 (See, e.g., Kuhlman et al., Science 302, 1364-1368 (2003)) and the core domain of the human tumor suppressor protein p53 (residues 94-312) (See, e.g., Friedler et al., J Biol Chem 278, 24108-24112 (2003)) conferred ampicillin resistance to MC4100 cells. On the contrary, those known to be insoluble, namely PhoA, TraR, and the human testicular cancer antigen NY-ESO1 (See, e.g., Chen et al., Proc Natl Acad Sci USA 94, 1914-1918 (1997); Murphy et al., Prep Biochem Biotechnol 35, 119-134 (2005)) were not detected in the soluble cytoplasmic fraction and did not confer ampicillin resistance to MC4100 cells (FIG. 4, lanes 5-8). Interestingly, the highly soluble de novo-designed Top7 protein fusion with a structure not previously observed in nature (See, e.g., Kuhlman et al., Science 302, 1364-1368 (2003)) is transported by the Tat pathway and confers significant ampicillin resistance on cells.

Example 4

Analysis of Amyloid Beta-Peptide (Aβ42) Folding and Solubility

Figure 5:
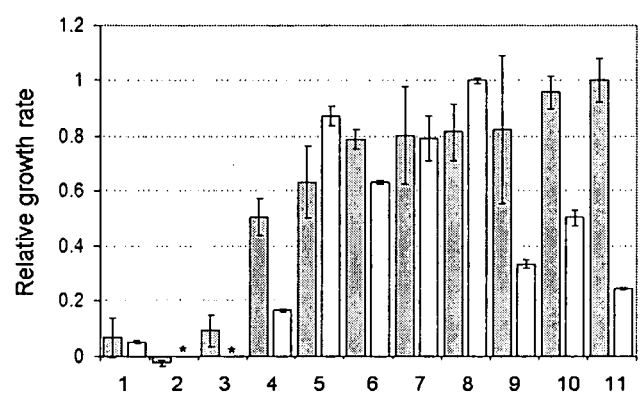
FIG. 5 shows an analysis of amyloid-beta peptide (Aβ42) and its derivatives. Relative growth rate of MC4100 cells as determined by 96-well plate liquid growth assays (gray bars) for the following target sequences: (1) wildtype Aβ42; (2) tandem repeat of Aβ42, Aβ-rpt; (3) Aβ42 F19P; (4) Aβ42 I32S (GM1); (5) Aβ42 V12E/V18E/M35T/I41N (GM3); (6) Aβ42 H6Q/V12A/V24A/I32M/V36G (GM11); (7) Aβ42 V12A/I32T/L34P (GM7); (8) Aβ42 F19S/L34P (GM6); (9) Aβ42 L34P (GM18); (10) Aβ42 F41/S8P/V24A/L34P (GM16); (11) Aβ42 F19S (GM19). Relative fluorescence of Aβ42-GFP fusions (white bars) was calculated by normalizing cell fluorescence for each fusion to that emitted from Aβ42 F19S/L34P (GM6).

To test whether the assay is effective in reporting solubility as related to misfolding and aggregation in human disease, the Alzheimer's amyloid beta-peptide Aβ42, which is the primary component of amyloid fibrils found in the brains of Alzheimer's patients (See, e.g., Selkoe, Physiol Rev 81, 741-766 (2001)) was analyzed using the folding assay of the present invention. The relative growth rates of *E. coli* cells expressing wildtype Aβ42 and a collection of Aβ42 mutants in the target position of pTMB (FIG. 5) were measured in the presence of ampicillin. In agreement with previously reported solubility data (See, e.g., Wigley et al., Nat Biotechnol 19, 131-136 (2001)), Aβ42(wt) did not confer growth to *E. coli* cells nor did a highly aggregation-prone tandem repeat of wt Aβ42 (See, e.g., Culvenor et al., Amyloid 5, 79-89 (1998)) (FIG. 5, lanes 1 and 2). In contrast, Aβ42 with proline substituted for phenylalanine in position 19 (F19P), a mutation known to retard fibril formation in vitro (See, e.g., Wood et al., Biochemistry 34, 724-730 (1995)), conferred a low level of ampicillin resistance (FIG. 5, lane 3). A panel of soluble Aβ42 variants was then screened which were previously isolated using a directed evolution strategy in combination with a GFP-based folding assay (See, e.g., Wurth et al., J Mol Biol 319, 1279-1290 (2002)). In general, the growth rate results (FIG. 5, gray bars) were in close agreement with the solubility reported by measuring the fluorescence emitted by *E. coli* cells expressing Aβ42-GFP fusion proteins (FIG. 5, white bars). Furthermore, the dynamic range of growth—comparing the growth of cells expressing the most soluble mutant to the growth of cells expressing wild-type Aβ42—was approximately 15-fold.

Example 5

Identification of Signal Peptides Capable of Tat Transport

A collection of 28 putative Tat signal peptides were identified using a bioinformatic algorithm. Specifically, a Hidden Markov Model (HMM) was constructed using a set of signal peptide sequences selected from experimentally confirmed Tat substrates (e.g., from *Escherichia coli* and *Pseudomonas aeruginosa*). The null model was taken as the empirical distribution of amino acids in positions 2 through 50 from the set of all annotated proteins in all complete bacterial genome sequences available from NCBI. These frequencies, along with the set of confirmed Tat leader peptide sequences, were used to create a hidden Markov model for the Tat motif using hmmbuild (See http://hmmer.wustl.edu/). The resulting Tat substrate model was used to search the annotated proteins from the chromosome of *E. coli* (GenBank accession NC_000913). All predicted substrates were crosschecked using the freely available signal peptide prediction tool SignalP (See http://www.cbs.dtu.dk/services/SignalP/).

Following identification of 28 putative Tat signals in *E. coli*, primers were used to PCR amplify the DNA encoding each individual signal peptide from the chromosome of *E. coli*. Each PCR product was ligated into an expression vector, just upstream of the gene encoding the *E. coli* maltose binding protein (MBP). The resulting collection of plasmids each express a putative Tat signal peptide N-terminally fused to MBP. Although a mechanism is not need to practice the present invention, and the present invention is not limited to any particular mechanism, it is contemplated that in some embodiments, the MBP protein is essential for metabolism of maltose. Thus, signal peptides capable of mediating Tat transport of MBP will bestow upon *E. coli* cells which lack a chromosomal copy of MBP (e.g. strain HS3018) the ability to metabolize maltose. On the contrary, when the Tat system is deleted in these cells (e.g. strain HS3018 ΔtatABCE) then maltose metabolism should be blocked. Using this strategy, 14 (of 28 total) signal peptides were identified that mediated Tat-specific transport of maltose binding protein (MBP) including the following: CueO, DmsA, FdnG, FdoG, HyaA, NapA, Sufl, TorA, WcaM, YagT, YcbK, YcdB, YdhX, YnfE (See Table 1, below). Interestingly, 5 signal peptides (AmiA, AmiC, FhuD, YaeI, YdcG) supported maltose metabolism in the presence and absence of the Tat machinery (tatABCE) indicating that these signal peptides were not exclusively Tat signals. Finally, a number of the Tat signals did not confer significant maltose metabolism under the conditions tested (HybA, HybO, NapG, NrfC, TorZ, YahJ, YedY, YfhG, YnfF) and are therefore not classified at present. Thus, in some embodiments, the strategy outlined above can be used to identify and confirm Tat signal peptides from any organism provided the genome sequence is available.

TABLE 1

Signal peptides capable of Tat transport

| Signal peptide | HS3018 | HS3018 ΔtatABCE |
|---|---|---|
| AmiA | ++ | ++ |
| AmiC | ++ | ++ |
| CueO | ++ | − |
| DmsA | + | − |
| FdnG | + | − |
| FdoG | + | − |
| FhuD | ++ | ++ |
| HyaA | ++ | − |
| HybA | +/− | +/− |
| HybO | +/− | + |
| NapA | + | − |
| NapG | +/− | +/− |
| NrfC | +/− | +/− |
| SufI | ++ | − |
| TorA (RR)* | ++ | − |
| TorA (KK)* | − | − |
| TorZ | +/− | +/− |
| WcaM | + | − |
| YaeI | ++ | ++ |
| YahJ | +/− | +/− |
| YagT | + | − |
| YcbK | ++ | − |
| YcdB | ++ | − |
| YdcG | ++ | ++ |
| YdhX | ++ | − |
| YedY | +/− | +/− |
| YfhG | +/− | +/− |
| YnfE | ++ | − |
| YnfF | +/− | +/− |

++ = bright red colonies, equivalent to MBP+ cells streaked on MacConkey
+ = red colonies but not as intense as MBP+ cells
+/− = pale red colonies
− = white colonies
 = Tat specific
*RR indicates a wild type RR-containing signal peptide while KK indicates a signal peptide where the RR amino acids were mutated to KK, a mutation known to abolish Tat transport.

Example 6

Effect of Molecular Chaperones on Tat Transport Efficiency

Figure 6:
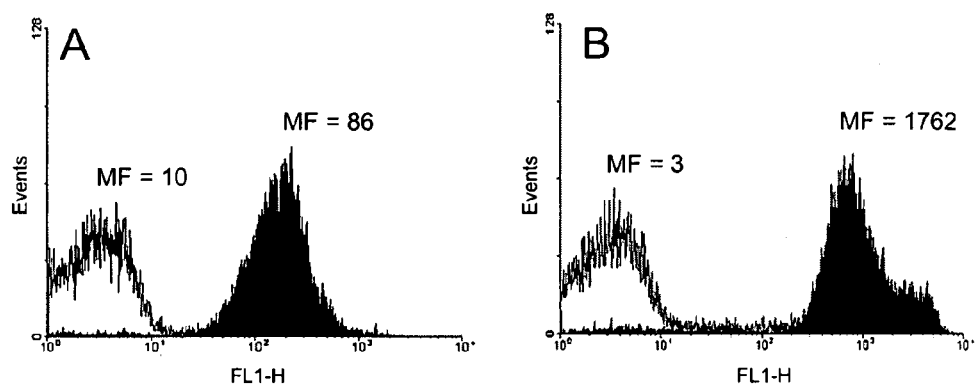
FIG. 6 depicts FACS generated fluorescence histograms of wildtype *E. coli* strain MC4100 (filled bars) and MC4100 dnaKdnaJ::kan mutant (empty bars) expressing (A) ssTorA-GFP-SsrA and (B) ssTorA-GFP. MF=mean fluorescence, FL1-H=fluorescence intensity

In order to identify the role that cytoplasmic chaperones play in Tat transport, a collection of chaperone mutant strains were tested for their ability to transport the green fluorescent protein (GFP) through the Tat system. For these studies, two reporter proteins were used: the first was ssTorA-GFP-SsrA which is a tripartite fusion between the Tat-specific TorA signal peptide, GFP and a C-terminal SsrA degradation tag. Owing to the SsrA tag, this protein is rapidly degraded in the cytoplasm by the proteases ClpXP. Thus, it is contemplated that, in some embodiments, the fluorescence that emanates from cells expressing ssTorA-GFP-SsrA arises from GFP that has been successfully transported to the periplasm prior to degradation in the cytoplasm. A second reporter used was a long-lived version of GFP carrying an N-terminal TorA signal peptide (ssTorA-GFP). A collection of 16 chaperone mutant strains were transformed with plasmid pTGS (expressing ssTorA-GFP-SsrA) or pTG (expressing ssTorA-GFP). Cells were grown overnight, subcultured into shake flasks and induced with 0.01 mM IPTG. Following 4-6 hours of induction, 5 μL of induced cells were introduced to a flow cytometer and fluorescence histograms were captured (See FIG. 6). Mean fluorescence (MF) emitted from each mutant was compared to the MF emitted from the isogenic parental strain expressing either ssTorA-GFP-SsrA or ssTorA-GFP. Data was normalized by dividing the MF of the parent strain by the MF of the mutant. As a result, a value of ~1 indicates virtually no difference in Tat transport of GFP between the parent and the mutant strain, whereas a value >1 indicates that transport is reduced in the mutant relative to the parent and a value <1 indicates that transport is increased in the mutant relative to the parent. Data generated during the development of the invention provides that DnaK (See FIG. 6), GroELS and ClpAB have the most substantial effect on Tat transport as fluorescence ratios for both ssTorA-GFP-SsrA and ssTorA-GFP expression were >>1 (See Table 2 below). Data is reported as the ratio of mean fluorescence (MF) measured for wild type cells relative to MF for mutant cells measured (MF wt/MF mutant). Data was taken 6 h post induction with 0.01 mM IPTG. Values are the average of 3 replicate experiments. ND=not determined. All strains were derived from MC4100 unless otherwise noted.

TABLE 2

Fluorescence emission from chaperone mutants expressing Tat-targeted GFP

| Strain* | pMMB-TGS | pMMB-TG |
|---|---|---|
| ΔclpA::kan | 12.64 (68.52/5.42) | 372.10 (1596.3/4.29) |
| ΔclpB::kan | 3.42 (68.5/20.2) | 1.63 (1596.3/982.2) |
| degP::kan[1] | 0.89 (43.8/49.0) | 0.96 (845.5/884.1) |
| dnaK756 | 27.03 (78.4/2.9) | 289.15 (1665.5/5.76) |
| dnaJ259 | 1.19 (78.4/65.5) | 4.58 (1665.5/363.4) |
| ΔdnaKdnaJ::kan | 8.70 (85.6/9.8) | 599.46 (1762.42/2.90) |
| ftsH1(ts)[2] | 2.61 (66.2/25.4) | ND |
| ftsH3::kan[2] | 2.56 (338.0/132.1) | ND |
| groEL140[3] | 26.97 (147.8/5.5) | 4.21 (1446.0/342.9) |
| groES30[3] | 21.10 (147.8/7.0) | 5.67 (1446.0/254.8) |
| grpE280 | 4.41 (150.7/34.2) | 2.21 (1201.5/542.9) |
| ΔhtpG | 7.04 (45.7/6.5) | 1.09 (1596.3/1459.0) |
| ibpl::kan | 0.84 (68.5/81.2) | 0.96 (1733.0/1810.6) |
| lon::Tn10tet | 1.25 (68.5/54.8) | 2.29 (1732.6/756.3) |
| secB::Tn5 | 0.92 (45.7/49.6) | 1.17 (1459.0/1245.4) |
| tig::cm | 0.79 (28.6/36.2) | 1.04 (1998.9/1911.0) |

[1]parent = KS272
[2]parent = W3110
[3]parent = B178

Example 7

Methods for Reducing the C-Terminal Fusion Partner in Folding Assay

Figure 7:
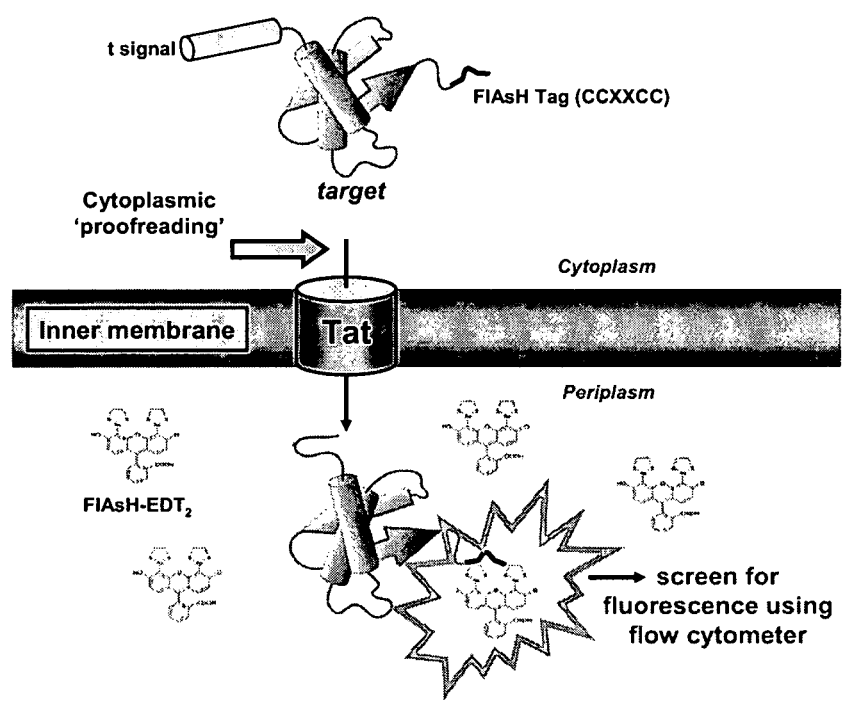
FIG. 7 shows the use of FlAsH labeling to minimize C-terminal fusion to target proteins in the expression constructs and folding assays of the present invention.

In some embodiments, the present invention utilizes a FACS-based method for monitoring folding and solubility using FlAsH labeling. Thus, in some embodiments, a 6 amino acid sequence known as a tetracycsteine FlAsH binding motif (—CCXXCC—, where C=cysteine and X=any amino acid) is used as a reporter (e.g., in place of a C-terminal β-lactamase gene sequence). The 6 amino acid motif is small in size (e.g., significantly smaller than β-lactamase) and is minimally invasive during the folding and subsequent translocation steps of the assays of the present invention. A schematic of one embodiment of this method is depicted is FIG. 7. For example, in some embodiments, if the ssTorA-target-FlAsH fusion protein is correctly folded, it will be transported by the Tat system to the periplasm. Once in the periplasm, the protein is accessible to the small, outer-membrane permeable ligand 4',5'-bis(1,3,2-dithioarsolan-2-yl)fluorescein, commonly referred to as FlAsH-EDT$_2$. This designed small ligand is nonfluorescent until it binds with high affinity and specificity to the tetracysteine domain (e.g., encoded and expressed by an expression construct comprising a target protein of the present invention). Such in situ labeling adds much less mass than does β-lactamase and offers greater versatility in attachment sites (e.g., on the N-terminus, C-terminus, or even embedded within a protein) as well as potential spectroscopic and chemical properties (e.g., for simple readout formats using microscopy or other visualization systems). Once E. coli cells expressing ssTorA-target-FlAsH have been labeled with the FlAsH-EDT$_2$ probe, the resulting fluorescent cells can easily be monitored and/or separated from non-fluorescent cells using a flow cytometer for fluorescence activated cell sorting (FACS). Use of the FlAsH tag provides the ability for de minimus modification of a target protein with the ability to identify the target protein from the other proteins inside live cells (e.g., through the ability to be fluorescently stained by small nonfluorescent dye molecules added from outside the cell).

Example 8

Figure 8:
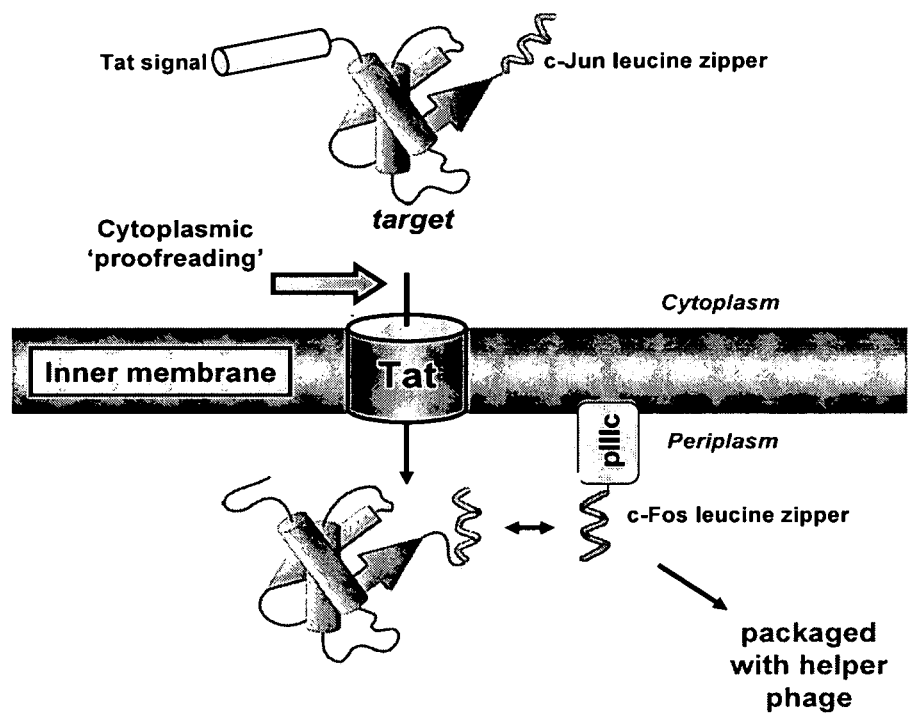
FIG. 8 shows the use of phage display to minimize C-terminal fusion to target proteins in the expression constructs and folding assays of the present invention.

A High-Throughput Screen for Monitoring Folding and Solubility Using Phage Display In some embodiments, the systems of the present invention can be modified in order that the C-terminal β-lactamase gene is replaced by a small leucine zipper protein (e.g., epitope grafted from the c-Jun protein). Such an epitope is small in size (e.g., significantly smaller in size than β-lactamase) and provides a minimally invasive epitope during the folding and subsequent translocation steps of assays of the present invention. In some embodiments, if the ssTorA-target-c-Jun protein is correctly folded, it will be transported into the periplasm (See FIG. 8). In some embodiments, a second protein fusion is co-expressed and is also localized to the periplasm via an alternate route (e.g., via the Sec pathway) such that its translocation will not interfere with transport of the target protein and will not be subject to proofreading. The second fusion protein consist of the filamentous phage coat protein (pIIIc) fused to the leucine zipper motif of the c-Fos protein. The leucine zipper domains of c-Jun and c-Fos interact in the periplasm, forming a stable complex between ssTorA-target-c-Jun and c-Fos-pIIIc. The complex is tethered to the periplasmic side of the inner membrane by virtue of the pIIIc protein. Next, filamentous helper phage are added to E. coli cells resulting in the formation of phage particles that have the target protein displayed on the head of the particle. These phage particles can be easily isolated from the bacteria. Importantly, the DNA encoding the target gene sequence is packaged inside the phage particle, thereby creating a link between the DNA sequence encoding the target protein and the expressed target protein displayed on the phage particle. A 6× histidine tag at the C-terminus of the ssTorA-target-c-Jun fusion protein allows affinity capture of folded target proteins displayed on the head of the phage particles (a process known as phage panning). Elution of bound phage followed by re-infection of bacteria and sequencing of the phage DNA allows rapid determination of the DNA sequence encoding the folded target protein. The premise for this strategy is that only correctly folded proteins will transit the Tat system and subsequently be assembled into phage particles. Thus, in preferred embodiments, the display of a target protein on the head of a phage particle is an indicator that the protein in question is correctly folded.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method for screening for mutations in a target protein sequence that is prone to misfolding or aggregation in the cytoplasm that alter solubility and/or folding of said target protein in the cytoplasm, comprising:
    a) introducing one or more mutations into the nucleic acid sequence that encodes said target protein;
    b) expressing the mutant target protein as a fusion protein in a host cell, wherein said fusion protein comprises a Tat leader signal, the target protein that is prone to misfolding or aggregation in the cytoplasm, and a selectable marker, wherein said fusion protein comprising a Tat leader signal, the target protein, and a selectable marker is translocated from the cytoplasm across a biological membrane into the periplasm as a correctly folded fusion protein as a requirement to confer selectable activity upon expression of said fusion protein by said host cell; and
    c) correlating expression of selectable activity with correct folding of the target protein in the cytoplasm, wherein said target protein is an antibody or antibody fragment.

2. The method of claim 1, wherein said method is used to screen a library of host cells comprising said fusion proteins comprising said mutations in said target protein.

3. A method for screening for mutations in a target protein sequence that is prone to misfolding or aggregation in the cytoplasm that alters solubility and/or folding of said target protein in the cytoplasm, comprising:
    a) providing a library of nucleic acid sequences encoding fusion proteins, wherein said fusion proteins each comprise a Tat leader signal, an altered target protein, and a selectable marker protein;
    b) expressing said fusion proteins in host cells, wherein said fusion protein comprising a Tat leader signal, the target protein that is prone to misfolding a aggregation in the cytoplasm, and a selectable marker is translocated from the cytoplasm across a biological membrane as a correctly folded fusion protein as a requirement to confer selectable activity upon expression of said fusion protein by said host cell; and
    c) correlating expression of selectable activity with correct folding of the target protein in the cytoplasm, wherein said target protein is an antibody or antibody fragment.

4. The method of claim 1, wherein said selectable marker is β-lactamase.

5. The method of claim 1, wherein said Tat leader signal is ssTorA.

6. The method of claim 1, wherein said translocation from the cytoplasm across a biological membrane is from the cytoplasm to the periplasm.

7. The method of claim 3, wherein said selectable marker is β-lactamase.

8. The method of claim 3, wherein said Tat leader signal is ssTorA.

9. The method of claim 3, wherein said translocation from the cytoplasm across a biological membrane is from the cytoplasm to the periplasm.

10. The method of claim 1, further comprising selecting host cells expressing the correctly folded target protein.

11. The method of claim 1, wherein said host cell is a prokaryotic host cell.

12. The method of claim 1, wherein said antibody fragment is an scFV.

13. The method of claim 3, wherein said antibody fragment is an scFV.

* * * * *

UNITED STATES PATENT AND TRADEMARK OFFICE
CERTIFICATE OF CORRECTION

PATENT NO. : 8,987,173 B2
APPLICATION NO. : 12/152482
DATED : March 24, 2015
INVENTOR(S) : Matthew P. DeLisa and Adam Charles Fisher Page 1 of 1

It is certified that error appears in the above-identified patent and that said Letters Patent is hereby corrected as shown below:

IN THE CLAIMS:

Column 54, line 45, should read:

target protein that is prone to misfolding or aggregation in

Signed and Sealed this
Fourteenth Day of July, 2015

Michelle K. Lee
*Director of the United States Patent and Trademark Office*